US012583821B2

(12) United States Patent
Cui et al.

(10) Patent No.: US 12,583,821 B2
(45) Date of Patent: Mar. 24, 2026

(54) SALT OF OMECAMTIV MECARBIL AND PROCESS FOR PREPARING SALT

(71) Applicant: Cytokinetics, Inc., South San Francisco, CA (US)

(72) Inventors: Sheng Cui, Thousand Oaks, CA (US); Henry Morrison, Thousand Oaks, CA (US); Karthik Nagapudi, South San Francisco, CA (US); Shawn D. Walker, Woodland Hills, CA (US); Charles Bernard, Moorpark, CA (US); Karl Bennett Hansen, Cohasset, MA (US); Neil Fred Langille, Thousand Oaks, CA (US); Alan Martin Allgeier, Wilmington, DE (US); Steven M. Mennen, Thousand Oaks, CA (US); Jacqueline C. S. Woo, Sherwood Park (CA); Bradley Paul Morgan, Moraga, CA (US); Alex Muci, San Francisco, CA (US)

(73) Assignee: CYTOKINETICS, INC., South San Francisco, CA (US)

( * ) Notice: Subject to any disclaimer, the term of this patent is extended or adjusted under 35 U.S.C. 154(b) by 0 days.

(21) Appl. No.: 18/421,849

(22) Filed: Jan. 24, 2024

(65) Prior Publication Data

US 2024/0317687 A1 Sep. 26, 2024

Related U.S. Application Data

(60) Continuation of application No. 17/448,833, filed on Sep. 24, 2021, now Pat. No. 11,958,809, which is a continuation of application No. 17/176,003, filed on Feb. 15, 2021, now abandoned, which is a continuation of application No. 16/920,155, filed on Jul. 2, 2020, now abandoned, which is a continuation of application No. 16/684,216, filed on Nov. 14, 2019, now abandoned, which is a continuation of application No. 15/963,529, filed on Apr. 26, 2018, now abandoned, which is a division of application No. 14/773,436, filed as application No. PCT/US2014/027146 on Mar. 14, 2014, now Pat. No. 9,988,354.

(60) Provisional application No. 61/785,763, filed on Mar. 14, 2013.

(51) Int. Cl.

| | |
|---|---|
| ***C07D 213/75*** | (2006.01) |
| ***A61K 9/20*** | (2006.01) |
| ***A61K 31/444*** | (2006.01) |
| ***A61K 31/496*** | (2006.01) |
| ***A61K 47/38*** | (2006.01) |
| ***A61P 9/00*** | (2006.01) |
| ***A61P 9/04*** | (2006.01) |
| ***A61P 9/06*** | (2006.01) |

(52) U.S. Cl.
CPC .......... *C07D 213/75* (2013.01); *A61K 9/2013* (2013.01); *A61K 9/2018* (2013.01); *A61K 9/2054* (2013.01); *A61K 31/496* (2013.01); *A61K 47/38* (2013.01)

(58) Field of Classification Search
CPC ................ C07D 213/75; A61K 31/496; A61K 31/444; A61K 47/38; A61P 9/00; A61P 9/04; A61P 9/06
See application file for complete search history.

(56) References Cited

U.S. PATENT DOCUMENTS

| | | | | |
|---|---|---|---|---|
| 6,531,469 | B1 | 3/2003 | Rieu et al. | |
| 7,507,735 | B2 | 3/2009 | Morgan et al. | |
| 7,989,455 | B2 | 8/2011 | Morgan et al. | |
| 8,101,617 | B2 | 1/2012 | Morgan et al. | |
| 8,110,595 | B2 | 2/2012 | Morgan et al. | |
| 8,445,495 | B2 | 5/2013 | Morgan et al. | |
| 8,513,257 | B2 | 8/2013 | Morgan et al. | |
| 8,871,768 | B2 | 10/2014 | Morgan et al. | |
| 8,871,769 | B2 | 10/2014 | Morgan et al. | |
| 9,150,564 | B2 | 10/2015 | Morgan et al. | |
| 9,643,925 | B2 | 5/2017 | Morgan et al. | |
| 9,895,308 | B2 * | 2/2018 | Caldwell | A61P 9/04 |
| 9,951,015 | B2 | 4/2018 | Bi et al. | |
| 9,988,354 | B2 | 6/2018 | Cui et al. | |
| 10,035,770 | B2 | 7/2018 | Morgan et al. | |
| 10,385,023 | B2 | 8/2019 | Morgan et al. | |
| 10,421,726 | B2 | 9/2019 | Bi et al. | |
| 10,543,215 | B2 | 1/2020 | Scott et al. | |
| 10,975,034 | B2 | 4/2021 | Morgan et al. | |
| 11,040,956 | B2 | 6/2021 | Caille et al. | |
| 11,384,053 | B2 | 7/2022 | Bi et al. | |

(Continued)

FOREIGN PATENT DOCUMENTS

| | | | |
|---|---|---|---|
| CN | 101035525 | A | 9/2007 |
| JP | 2002535329 | A | 10/2002 |

(Continued)

OTHER PUBLICATIONS

Decision of Technical Board of Appeal 3.3.02 of Mar. 7, 2024, dated Jun. 5, 2024, for European Patent No. 14720369.9/EP2970123, 24 pages.
Minutes of the Oral Proceeding T1107/22-3.3.02 3.3.02 of Mar. 7, 2024, for European Patent No. 14720369.9/EP2970123, 9 pages.
Newman, A. (Sep./Oct. 2011). "X-ray Powder Diffraction in Solid Form Screening and Selection", American Pharmaceutical Review Sep./Oct. (6):44-51.
U.S. Appl. No. 18/939,410, filed Nov. 6, 2024, by Elena Brasola et al. (A copy of the U.S. Patent Application is not submitted herewith pursuant to the waiver of 37 C.F.R. § 1.98(a)(2)(iii) issued by the Office on Sep. 21, 2004.).

(Continued)

*Primary Examiner* — Sun Jae Yoo
(74) *Attorney, Agent, or Firm* — MORRISON & FOERSTER LLP

(57) ABSTRACT

Provided are omecamtiv mecarbil dihydrochloride salt forms, compositions and pharmaceutical formulations thereof, and methods for their preparation and use.

8 Claims, 7 Drawing Sheets

(56) References Cited

U.S. PATENT DOCUMENTS

| | | | |
|---|---|---|---|
| 11,465,969 | B2 | 10/2022 | Morrison et al. |
| 11,472,773 | B2 | 10/2022 | Cui et al. |
| 11,576,910 | B2 | 2/2023 | Honarpour et al. |
| 11,702,380 | B2 | 7/2023 | Caille et al. |
| 11,753,394 | B2 | 9/2023 | Caille et al. |
| 11,884,630 | B2 | 1/2024 | Bi et al. |
| 11,926,592 | B2 | 3/2024 | Morrison |
| 11,931,358 | B2 | 3/2024 | Honarpour |
| 11,958,809 | B2 | 4/2024 | Cui |
| 11,986,474 | B1 | 5/2024 | Malik et al. |
| 12,162,815 | B2 | 12/2024 | Brasola et al. |
| 12,194,039 | B2 | 1/2025 | Honarpour et al. |
| 12,221,417 | B2 | 2/2025 | Cui et al. |
| 12,264,133 | B2 | 4/2025 | Morgan et al. |
| 12,269,811 | B2 | 4/2025 | Caille et al. |
| 12,275,704 | B2 | 4/2025 | Bi et al. |
| 12,295,952 | B2 | 5/2025 | Honarpour et al. |
| 2005/0096296 | A1 | 5/2005 | Fikstad et al. |
| 2006/0014761 | A1 | 1/2006 | Morgan et al. |
| 2007/0161617 | A1 | 7/2007 | Morgan et al. |
| 2007/0208000 | A1 | 9/2007 | Morgan et al. |
| 2008/0266044 | A1 | 10/2008 | Nicoletti |
| 2009/0036447 | A1 | 2/2009 | Morgan et al. |
| 2009/0099198 | A1 | 4/2009 | Morgan et al. |
| 2009/0192168 | A1 | 7/2009 | Muci et al. |
| 2010/0029680 | A1 | 2/2010 | Morgan et al. |
| 2010/0087500 | A1 | 4/2010 | Stover |
| 2011/0182947 | A1 | 7/2011 | Appel et al. |
| 2012/0172372 | A1 | 7/2012 | Morgan et al. |
| 2013/0324549 | A1 | 12/2013 | Morgan et al. |
| 2014/0038983 | A1 | 2/2014 | Morgan et al. |
| 2014/0309235 | A1 | 10/2014 | Bi et al. |
| 2015/0005296 | A1 | 1/2015 | Morgan et al. |
| 2016/0015628 | A1 | 1/2016 | Caldwell |
| 2016/0016906 | A1 | 1/2016 | Cui et al. |
| 2016/0115133 | A1 | 4/2016 | Morgan et al. |
| 2017/0267638 | A1 | 9/2017 | Morgan et al. |
| 2018/0140611 | A1 | 5/2018 | Scott et al. |
| 2018/0273479 | A1 | 9/2018 | Bi et al. |
| 2018/0305316 | A1 | 10/2018 | Morgan et al. |
| 2018/0312469 | A1 | 11/2018 | Cui et al. |
| 2019/0352267 | A1 | 11/2019 | Morgan et al. |
| 2020/0079736 | A1 | 3/2020 | Cui et al. |
| 2020/0108076 | A1 | 4/2020 | Scott et al. |
| 2020/0155547 | A1 | 5/2020 | Honarpour et al. |
| 2020/0277261 | A1 | 9/2020 | Bi et al. |
| 2020/0308143 | A1 | 10/2020 | Caille et al. |
| 2020/0331859 | A1 | 10/2020 | Cui et al. |
| 2020/0399221 | A1 | 12/2020 | Cui et al. |
| 2021/0198203 | A1 | 7/2021 | Morgan et al. |
| 2021/0221771 | A1 | 7/2021 | Morrison et al. |
| 2021/0292271 | A1 | 9/2021 | Brasola et al. |
| 2021/0371397 | A1 | 12/2021 | Caille et al. |
| 2022/0042055 | A1 | 2/2022 | Bisagni et al. |
| 2022/0153700 | A1 | 5/2022 | Cui et al. |
| 2022/0184068 | A1 | 6/2022 | Honarpour et al. |
| 2022/0185779 | A1 | 6/2022 | Morgan et al. |
| 2022/0298114 | A1 | 9/2022 | Bi et al. |
| 2023/0044617 | A1 | 2/2023 | Cui et al. |
| 2023/0090391 | A1 | 3/2023 | Bi et al. |
| 2023/0108971 | A1 | 4/2023 | Morrison et al. |
| 2023/0149394 | A1 | 5/2023 | Honarpour et al. |
| 2023/0355615 | A1 | 11/2023 | Honarpour et al. |
| 2023/0373955 | A1 | 11/2023 | Caille et al. |
| 2024/0101517 | A1 | 3/2024 | Cui |
| 2024/0199550 | A1 | 6/2024 | Morrison et al. |
| 2024/0217933 | A1 | 7/2024 | Bi et al. |
| 2025/0163023 | A1 | 5/2025 | Caille et al. |
| 2025/0179005 | A1 | 6/2025 | Brasola et al. |
| 2025/0205228 | A1 | 6/2025 | Honarpour et al. |
| 2025/0243163 | A1 | 7/2025 | Cui et al. |
| 2025/0255862 | A1 | 8/2025 | Honarpour et al. |

FOREIGN PATENT DOCUMENTS

| | | | |
|---|---|---|---|
| JP | 2005507909 | A | 3/2005 |
| JP | 2007510658 | A | 4/2007 |
| JP | 2008503467 | A | 2/2008 |
| JP | 2009516000 | A | 4/2009 |
| JP | 2009519951 | A | 5/2009 |
| JP | 2011520837 | A | 7/2011 |
| JP | 2016502348 | A | 1/2016 |
| WO | 2003032956 | A1 | 4/2003 |
| WO | 2003032965 | A2 | 4/2003 |
| WO | 2005041929 | A1 | 5/2005 |
| WO | 2006009726 | A2 | 1/2006 |
| WO | 2006009726 | A3 | 11/2006 |
| WO | 2007054975 | A1 | 5/2007 |
| WO | 2007059500 | A2 | 5/2007 |
| WO | 2007070683 | A2 | 6/2007 |
| WO | 2007059500 | A3 | 11/2007 |
| WO | 2009138438 | A1 | 11/2009 |
| WO | 2014085336 | A1 | 6/2014 |
| WO | 2014152270 | A1 | 9/2014 |
| WO | 2020011626 | A1 | 1/2020 |
| WO | 2020014406 | A1 | 1/2020 |
| WO | 2021053175 | A1 | 3/2021 |
| WO | 2021053189 | A1 | 3/2021 |
| WO | 2021070123 | A1 | 4/2021 |
| WO | 2021070124 | A1 | 4/2021 |
| WO | 2021136477 | A1 | 7/2021 |
| WO | 2022177927 | A1 | 8/2022 |

OTHER PUBLICATIONS

U.S. Appl. No. 18/642,005, filed Apr. 22, 2024, by Fady Malik et al. (U.S. Patent Application is not submitted herewith pursuant to the waiver of 37 C.F.R. § 1.98(a)(2)(iii) issued by the Office on Sep. 21, 2004.).

U.S. Appl. No. 18/967,331, filed Dec. 3, 2024, by Narimon Honarpour et al. (U.S. Patent Application is not submitted herewith pursuant to the waiver of 37 C.F.R. § 1.98(a)(2)(iii) issued by the Office on Sep. 21, 2004.).

U.S. Appl. No. 18/990,483, filed Dec. 20, 2024, by Sheng Cui et al. (A copy of the U.S. Patent Application is not submitted herewith pursuant to the waiver of 37 C.F.R. § 1.98(a)(2)(iii) issued by the Office on Sep. 21, 2004.).

U.S. Appl. No. 19/029,911, filed Jan. 17, 2025, by Bi Mingda et al. (U.S. Patent Application is not submitted herewith pursuant to the waiver of 37 C.F.R. § 1.98(a)(2)(iii) issued by the Office on Sep. 21, 2004.).

U.S. Appl. No. 19/029,945, filed Jan. 17, 2025, by Caille Sebastien et al. (U.S. Patent Application is not submitted herewith pursuant to the waiver of 37 C.F.R. § 1.98(a)(2)(iii) issued by the Office on Sep. 21, 2004.).

Amendment in Response to Non-Final Office Action under 37 C.F.R. 1.111, dated Feb. 2, 2017 for U.S. Appl. No. 14/773,436, filed Sep. 8, 2015, 6 pages.

Anonymous. (2021). "Technical Report on Effects of OM Entities: Comparing the Physical Stability of OM Entities," as submitted by patent proprietor Amgen and Cytokinetics, Inc. in a letter dated Aug. 1, 2021, 22 pages.

Badawy, S.I.F. et al. (May 2007). "Microenvironmental pH Modulation in Solid Dosage Forms," Journal of Pharmaceutical Sciences 96(5):948-959.

Berge, S.M. et al. (Jan. 1977). "Pharmaceuticals Salts," J. Pharmaceutical Sciences 66(1):1-19.

Brief Communication containing a Letter from the Proprietor of the Patent of Jan. 8, 2021 and Auxiliary Requests 1-7, from the EPO in EP2970123 dated Jan. 19, 2021, 62 pages.

Brief Communication regarding the Oral Proceedings and containing a Letter from the Opponent submitted Dec. 7, 2021, in the Opposition of EP Application No. EP14720369.9/EP2970123, 28 pages.

Brief Communication regarding the Oral Proceedings and containing a Letter from the Proprietor and Auxiliary Request 8-13,

(56) References Cited

OTHER PUBLICATIONS submitted Dec. 13, 2021, in the Opposition of EP Application No. EP14720369.9/EP2970123, 47 pages.
Brief Communication regarding the Oral Proceedings and containing a Letter from the Proprietor submitted Oct. 15, 2021, in the Opposition of EP Application No. EP14720369.9/EP2970123, 8 pages.
Brittain, H.G. (2008). Theory and Origin of Polymorphism in Polymorphism in Pharmaceutical Solids, Brittain eds Marcel Decker, Inc., NY, NY, pp. 17-18, 4 pages.
Caira, M.R. (1998). "Crystalline Polymorphism of Organic Compounds," in Design of Organic Solids. Topics in Current Chemistry, 198:163-208.
Carstensen, Advanced Pharmaceutical Solids, Drugs and Pharmaceutical Sciences, 110 New York: Marcel Dekker, Inc. (2001).
Chawla, G. et al. (Jan.-Mar. 2004). "Challenges in Polymorphism of Pharmaceuticals", GRIPS 5(1):9-12.
Cleland, J.G.F. et al. (Aug. 20, 2011). "The Effects Of The Cardiac Myosin Activator, Omecamtivmecarbil, On Cardiac Function In Systolic Heart Failure: A Double-Blind, Placebo Controlled, Crossover, Dose-Ranging Phase 2 Trial," Lancet 378:676-683.
Colorcon (2009). "An Introduction to METHOCEL, Premium Cellulose Esthers," Colorcon, Version 2, 2 pages.
Communication of a Notice Opposition mailed May 20, 2020, signed May 14, 2020, by Opponent Keltie LLP against Granted European Patent Application EP14720369.9/EP2970123, filed by Amgen Inc. and Cytokinetics, 27 pages.
Communication of Summons to attend Oral Proceedings Pursuant to Rule 115(1)EPC (including Annex to the communication) in the opposition of EP Application No. EP14720369.9/EP2970123, mailed Mar. 30, 2021 11 pages.
Communication of the Board of Appeals Pursuant to Article 15(1) of the Rules of Procedure of the Board of Appeals, mailed Jan. 19, 2024, for EP Application No. EP14720369.9/EP2970123, 16 pages.
Declaration of Chunsheng QIAO for EP 2970123 dated and signed Oct. 14, 2021, 5 pages.
Declaration of Fady Malik for EP 2970123 dated and signed Dec. 13, 2021, 3 pages.
Declaration of Mingda Bi for EP 2970123 dated Jul. 1, 2021, 2 pages.
Declaration under 37 CFR 1.132 by inventor Mingda Bi dated and signed Jan. 12, 2016, for U.S. Appl. No. 14/210,713, filed Mar. 14, 2014, 4 pages.
Devane, J. (Mar. 8, 2013). "Impact of IVIVR on Product Development," in In Vitro-in Vivo Correlations, Young, D. B. et al.eds., p. 246, 1 page.
Dow. (Jul. 2000). "Using METHOCEL Cellulose Ethers for Controlled Releiase of Drugs in Hydrophilic Matrix Systems," WEB Brochure, located at https://www.colorcon.com/products-formulation/all-products/polymers-controlled-release/hydrophilic-matrix-tablets/methocel-dc2/download/677/2063/34, last visited on Jan. 28, 36 pages.
Dow. "METHOCEL Cellulose Ethers, Technical Handbook", located at https://cms.chempoint.com/ic/getattachment/2d8a4ff1-a232-46b7-b47d-956f2753cb3b/attachment.aspx last visited on Nov. 5, 2021, 32 pages.
European Search Report and Search Opinion for EP Patent Application No. EP20201011.2, filed Oct. 9, 2020, mailed Apr. 13, 2021, 8 pages.
Grounds of Appeal dated Jun. 20, 2022, for European Patent No. 2970123, Carpmaels & Ransford, Proprietors: Amgen Inc. and Cytokinteics, Inc. and Opponent Keltie LLP, 49 pages.
Grounds of Appeal dated Jun. 20, 2022, for European Patent No. 2970123, Opponent Keltie LLP, Patentee Amgen Inc. and Cytokinetics, Inc., 32 pages.
Gu et al., Grouping solvents by statistical analysis of solvent property parameters: Implication to polymorph screeninQ. Int. J. Pharmaceut. 283: 117-25 (2004).
Hellriegel, E.T. et al. (Dec. 1996). "Commentaries Interpatient Variability in Bioavailability is related to the extent of absorption: Implications for the Bioavailability and Bioequivalence Studies," Clinical Pharmacology & Therapeutics 60(6):601-607.
Hirayama, Organic Crystal production Manual: Principle and Know-How, Maruzen CO. Ltd. Japan (2008), 28 pages, no English abstract available.
Interlocutory Decision in Opposition Proceedings (Art. 101(3)(A) and 106(2) EPC), for European Application No. EP14720369.9/EP2970123, dated Feb. 10, 2022, 74 pages.
International Preliminary Report on Patentability issue date of Sep. 15, 2015, for Patent Application No. PCT/US2014/027104, filed Mar. 14, 2014, 7 pages.
International Preliminary Report on Patentability issue date of Sep. 15, 2015, for Patent Application No. PCT/US2014/027146, filed Mar. 14, 2014, 7 pages.
International Search Report and Written Opinion of the International Searching Authority in connection with International Application No. PCT/US2014/027104, United States Patent Office, dated Mar. 14, 2015, 9 pages.
International Search Report and Written Opinion of the International Searching Authority in connection with International Application No. PCT/US2014/027146, United States Patent Office, dated Mar. 14, 2014, 10 pages.
James, U.S. (Aug. 7, 1998). "Ritonavir Capsule Manufacturing Problems Will Require Switch To Liquid Formulation," AIDS Treat News 300(1), Abstract Only, 1 page.
Malik, Fady, curriculum vitae dated Nov. 2021, 13 pages.
Minamivamado (Apr. 25, 1984). New pharmaceutics, pp. 102-103 and 232-233, 5 pages.
Newman et al., "Solid-state analysis of the active pharmaceutical ingredient in drug products", DDT vol. 8, No. 19, Oct. 2003, p. 898-905.
Office Action issued in connection with Japanese Patent Application No. 2016-502348, dated Dec. 12, 2017.
Preliminary Communication about the Results of Oral Proceedings mailed Dec. 16, 2021, for EP Application No. EP14720369.9/EP2970123, 9 pages.
Reply to Appeal dated Nov. 4, 2022, for European Patent No. 2970123, Carpmaels & Ransford, Proprietors: Amgen Inc. and Cytokinteics, Inc. and Opponent Keltie LLP, 84 pages.
Reply to Notice of Appeal dated Nov. 4, 2022, for European Patent No. 2970123, Opponent Keltie LLP, Patentee Amgen Inc. And Cytokinetics, Inc., 112 pages.
Response to the Summons to Oral Proceedings mailed on Oct. 31, 2023, for EP Application No. EP14720369.9/EP2970123, 4 pages.
Rowe, R. C. et al. (2006). Handbook of Pharmaceutical Excipient, 5th edition, Pharmaceutical Press, 945 pages.
Second Declaration Under 37 CFR 1.132 of Mingda Bi, dated Jun. 24, 2016, 4 pages.
Siepe et al., "Strategies for the Design of Hydrophilic Matrix Tablets with Controlled 1 Microenvironmental oH", Int. J. Pharm., 316(1-2):14-20 (2006).
Stahly, Journal of Pharmaceutical Science and Technology, Japan, 66(6):435-439 (2006). (No English Abstract Available).
Teerlink, J.R (Dec. 2009, e-pub. Feb. 21, 2009). "A Novel Approach to Improve Cardiac Performance: Cardiac Myosin Activators", Heart Fail Rev. 14(4):289-298.
Teerlink, J.R. et al. (Aug. 20, 2011). "Dose-Dependent Augmentation Of Cardiac Systolic Function With The Selective Cardiac Myosin Activator, Omecamtiv Mecarbil: A First-In-Man Study," Lancet 378(9792):667-675.
U.S. Appl. No. 15/898,303, filed Feb. 16, 2018, by William Brett Caldwell et al. (U.S. Patent Application is not submitted herewith pursuant to the waiver of 37 C.F.R. § 1.98(a)(2)(iii) issued by the Office on Sep. 21, 2004.).
U.S. Appl. No. 17/176,003, filed Feb. 15, 2021, by Sheng Cui et al. (U.S. Patent Application is not submitted herewith pursuant to the waiver of 37 C.F.R. § 1.98(a)(2)(iii) issued by the Office on Sep. 21, 2004.).
U.S. Appl. No. 18/416,741, filed Jan. 18, 2024, by Henry Morrison et al. (U.S. Patent Application is not submitted herewith pursuant to the waiver of 37 C.F.R. § 1.98(a)(2)(iii) issued by the Office on Sep. 21, 2004.).

(56) References Cited

OTHER PUBLICATIONS

U.S. Appl. No. 18/531,424, filed Dec. 6, 2023, by Mingda Bi et al. (U.S. Patent Application is not submitted herewith pursuant to the waiver of 37 C.F.R. § 1.98(a)(2)(iii) issued by the Office on Sep. 21, 2004.).
Mnogradova, E.V. et al. (Jul. 11, 2012). "Palladium-Catalyzed Cross-Coupling of Aryl Chlorides and Triflates with Sodium Cyanate: A Practical Synthesis of Unsymmetrical Ureas," J. Am. Chem. Soc. 134(27):11132-11135, 11 pages.
Waggoner, P. (2020). "Average Relative Humidity," Encyclopedia Britannica, as retrieved on Dec. 29, 2020, 4 pages.
WHO (2009). "Stability Testing Of Active Pharmaceutical Ingredients And Finished Pharmaceutical Products," 43rd Report, Annex 2 in the World Health Organization (WHO) Technical Report Series, No. 953, 34 pages.
Brief Communication regarding the Interlocutory decision in Opposition proceedings dated Jun. 4, 2025, in the Opposition of EP Application No. EP14720369.9/EP2970123, 35 pages.
Notice of Pre-Grant Opposition mailed Nov. 24, 2025, for Indian Patent Application No. 3414/KOLNP/2015 and Written Opposition, 40 pages.

* cited by examiner

SALT OF OMECAMTIV MECARBIL AND PROCESS FOR PREPARING SALT

CROSS REFERENCE TO RELATED APPLICATIONS

This application is continuation of U.S. application Ser. No. 17/448,833, filed Sep. 24, 2021, which is a continuation of U.S. application Ser. No. 17/176,003, filed Feb. 15, 2021, which is a continuation of U.S. application Ser. No. 16/920,155, filed Jul. 2, 2020, which is a continuation of U.S. application Ser. No. 16/684,216, filed Nov. 14, 2019, which is a continuation of U.S. application Ser. No. 15/963,529, filed Apr. 26, 2018, which is a divisional of U.S. application Ser. No. 14/773,436, which adopts an international filing date of Mar. 14, 2014, now U.S. Pat. No. 9,988,354, which is the national stage application under 35 U.S.C. § 371 of International Application No. PCT/US2014/027146, filed internationally on Mar. 14, 2014, which claims benefit of U.S. Provisional Application 61/785,763, filed Mar. 14, 2013.

FIELD

Provided are omecamtiv mecarbil dihydrochloride polymorph forms, methods of making omecamtiv mecarbil, including omecamtiv mecarbil dihydrochloride polymorph forms, compositions comprising omecamtiv mecarbil dihydrochloride polymorph forms, and methods of using omecamtiv mecarbil dihydrochloride salt polymorph forms.

BACKGROUND

The cardiac sarcomere is the basic unit of muscle contraction in the heart. The cardiac sarcomere is a highly ordered cytoskeletal structure composed of cardiac muscle myosin, actin and a set of regulatory proteins. The discovery and development of small molecule cardiac muscle myosin activators would lead to promising treatments for acute and chronic heart failure. Cardiac muscle myosin is the cytoskeletal motor protein in the cardiac muscle cell. It is directly responsible for converting chemical energy into the mechanical force, resulting in cardiac muscle contraction.

Current positive inotropic agents, such as beta-adrenergic receptor agonists or inhibitors of phosphodiesterase activity, increase the concentration of intracellular calcium, thereby increasing cardiac sarcomere contractility. However, the increase in calcium levels increase the velocity of cardiac muscle contraction and shortens systolic ejection time, which has been linked to potentially life-threatening side effects. In contrast, cardiac muscle myosin activators work by a mechanism that directly stimulates the activity of the cardiac muscle myosin motor protein, without increasing the intracellular calcium concentration. They accelerate the rate-limiting step of the myosin enzymatic cycle and shift it in favor of the force-producing state. Rather than increasing the velocity of cardiac contraction, this mechanism instead lengthens the systolic ejection time, which results in increased cardiac muscle contractility and cardiac output in a potentially more oxygen-efficient manner.

U.S. Pat. No. 7,507,735, herein incorporated by reference, discloses a genus of compounds, including omecamtiv mecarbil (AMG 423, CK-1827452), having the structure:

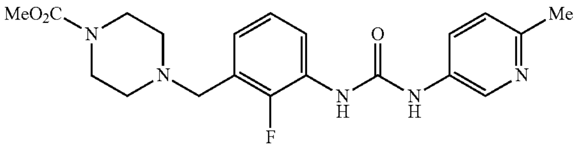 [SMILES: COC(=O)N1CCN(Cc2cccc(NC(=O)Nc3ccc(C)nc3)c2F)CC1]

Omecamtiv mecarbil is a first in class direct activator of cardiac myosin, the motor protein that causes cardiac contraction. It is being evaluated as a potential treatment of heart failure in both intravenous and oral formulations with the goal of establishing a new continuum of care for patients in both the in-hospital and outpatient settings.

Because drug compounds having, for example, improved stability, solubility, shelf life, and in vivo pharmacology, are consistently sought, there is an ongoing need for new or purer salts, hydrates, solvates, and polymorphic crystalline forms of existing drug molecules. The crystalline forms of omecamtiv mecarbil described herein help meet this and other needs.

SUMMARY

Provided is a dihydrochloride form of omecamtiv mecarbil.

Also provided is omecamtiv mecarbil dihydrochloride hydrate.

Also provided is a crystalline form of a dihydrochloride form of omecamtiv mecarbil.

Also provided is omecamtiv mecarbil dihydrochloride hydrate Form A.

Also provided is anhydrous omecamtiv mecarbil dihydrochloride.

Also provided is anhydrous omecamtiv mecarbil dihydrochloride Form B.

Also provided is anhydrous omecamtiv mecarbil dihydrochloride Form C.

Also provided are composition and pharmaceutical compositions comprising a dihydrochloride form of omecamtiv mecarbil.

Also provided is a method of preparing omecamtiv mecarbil comprising admixing methyl 4-(3-amino-2-fluorobenzyl)piperazine-1-caboxylate and phenyl (6-methylpyridin-3-yl) carbamate in the presence of a trialkylamine base to form omecamtiv mecarbil.

Also provided is a method of preparing omecamtiv mecarbil dihydrochloride hydrate comprising:

(a) hydrogenating methyl 4-(2-fluoro-3-nitrobenzyl)piperazine-1-carboxylate in the presence of a hydrogenation catalyst to form methyl 4-(3-amino-2-fluorobenzyl)piperazine-1-caboxylate;

(b) admixing methyl 4-(3-amino-2-fluorobenzyl)piperazine-1-caboxylate and phenyl (6-methylpyridin-3-yl)carbamate in the presence of a trialkylamine base to form omecamtiv mecarbil as a free base; and (c) crystallizing the omecamtiv mecarbil free base in the presence of aqueous hydrochloric acid and an alcohol solvent to form omecamtiv mecarbil dihydrochloride hydrate salt.

DETAILED DESCRIPTION

Figure 1:
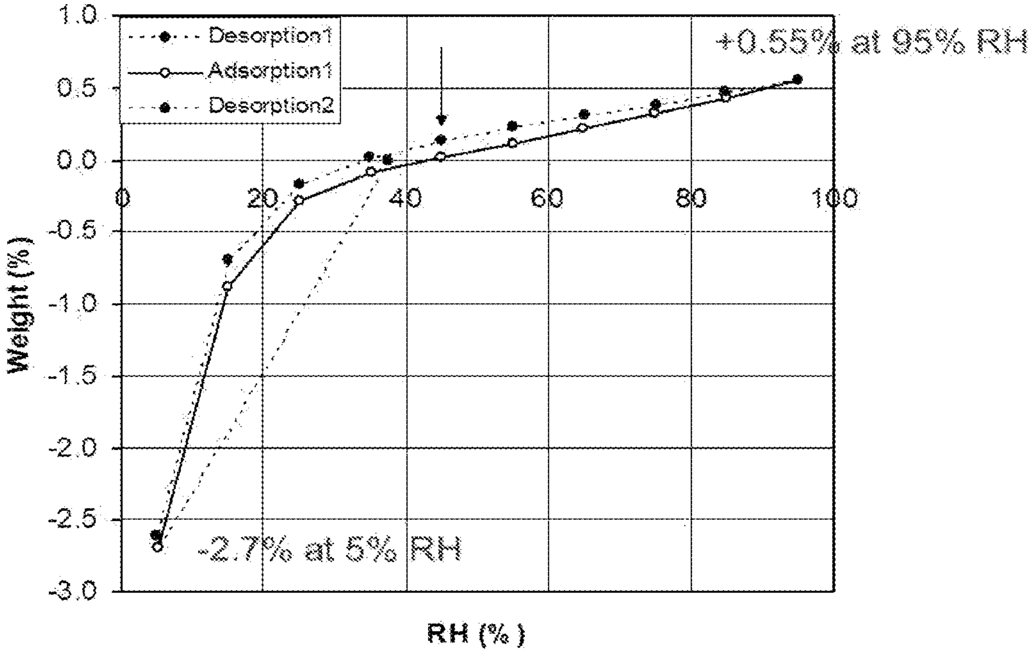
FIG. 1 shows the dynamic vapor sorption of a omecamtiv mecarbil dihydrochloride hydrate form, Form A.

Unless otherwise specified, the following definitions apply to terms found in the specification and claims:

"Treatment" or "treating" means any treatment of a disease in a patient, including: a) preventing the disease, that is, causing the clinical symptoms of the disease not to develop; b) inhibiting the disease; c) slowing or arresting the development of clinical symptoms; and/or d) relieving the disease, that is, causing the regression of clinical symptoms. Treatment of diseases and disorders herein is intended to also include the prophylactic administration of a pharmaceutical formulation described herein to a subject (i.e., an animal, preferably a mammal, most preferably a human) believed to be in need of preventative treatment, such as, for example, chronic heart failure.

The term "therapeutically effective amount" means an amount effective, when administered to a human or non-human patient, to treat a disease, e.g., a therapeutically effective amount may be an amount sufficient to treat a disease or disorder responsive to myosin activation. The therapeutically effective amount may be ascertained experimentally, for example by assaying blood concentration of the chemical entity, or theoretically, by calculating bioavailability.

"Pharmaceutically acceptable salts" include, but are not limited to salts with inorganic acids, such as hydrochlorate (i.e., hydrochloride), phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, $HOOC-(CH_2)_n-COOH$ where n is 0-4, and like salts. Similarly, pharmaceutically acceptable cations include, but are not limited to sodium, potassium, calcium, aluminum, lithium, and ammonium. Those skilled in the art will recognize various synthetic methodologies that may be used to prepare non-toxic pharmaceutically acceptable addition salts.

As used herein, the term "polymorphs" or "polymorphic forms" refers to crystal forms of the same molecule. Different polymorphic forms of a molecule have different physical properties as a result of the arrangement or conformation of the molecules in the crystal lattice. Some of the different physical properties include melting temperature, heat of fusion, solubility, dissolution rate, and/or or vibrational spectra. The physical form of a particular compound is particularly important when the compound is used in a pharmaceutical formulation because different solid forms of a compound result in different properties of the drug product.

Polymorphs of a molecule can be obtained by a number of methods, as shown in the art, such as, for example, melt recrystallization, melt cooling, solvent recrystallization, desolvation, rapid evaporation, rapid cooling, slow cooling, vapor diffusion, and sublimation. Techniques for characterizing a polymorph include X-ray powder diffraction (XRPD), single crystal X-ray diffraction (XRD), differential scanning calorimetry (DSC), vibrational spectroscopy (e.g., IR and Ram spectroscopy), solid state nuclear magnetic resonance (ssNMR), hot stage optical microscopy, scanning electron microscopy (SEM), electron crystallography and quantitative analysis, particle size analysis (PSA), surface area analysis, solubility studies, and dissolution studies.

The term "hydrate" refers to the chemical entity formed by the interaction of water and a compound.

As used herein, the term "monohydrate" refers a hydrate that contains one molecule of water per one molecule of the substrate.

As used herein, the term "crystalline" refers to a solid in which the constituent atoms, molecules, or ions are arranged in a regularly ordered, repeating pattern in three dimensions.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

Provided is a dihydrochloride hydrate form of omecamtiv mecarbil. In various embodiments of this aspect, the dihydrochloride hydrate form of omecamtiv mecarbil is crystalline (Form A). Embodiments of the dihydrochloride hydrate form of omecamtiv mecarbil can be characterized by one or more of the parameters described in further detail below.

The dihydrochloride hydrate form of omecamtiv mecarbil has a water solubility of greater than 40 mg/mL at a pH in a range of about 3.5. Further, Form A is non-hygroscopic. For example, when subjected to dynamic vapor sorption, Form A demonstrated a total weight gain of about 0.55 wt. % between about 40% and about 95% relative humidity (RH) and weight loss of about 2.7 wt % between about 30% and about 5% RH. In some embodiments, the dihydrochloride hydrate form of omecamtiv mecarbil has a dynamic vapor sorption profile substantially as shown in FIG. 1 wherein by "substantially" is meant that the reported DVS features can vary by about ±5% RH.

The dynamic vapor sorption indicates that the salt dehydrates when dried to 5% relative humidity, but almost fully re-hydrates by 15% relative humidity. Above 15% relative humidity, the sample is non-hygroscopic, showing only about a 1.0% weight change upon reaching 95% relative humidity. No phase change occurred after the vapor sorption experiment when examined by XRPD.

Water solubility for Form A was determined to be greater than 40 mg/mL (pH=3.5) with no phase change occurring during the 24 hour slurry experiment when examined by XRPD. Further still, Form A is stable under accelerated stability testing conditions. For example, Form A remains in substantially the same physical form over 6 months at 40° C. and 75% RH.

Figure 2:
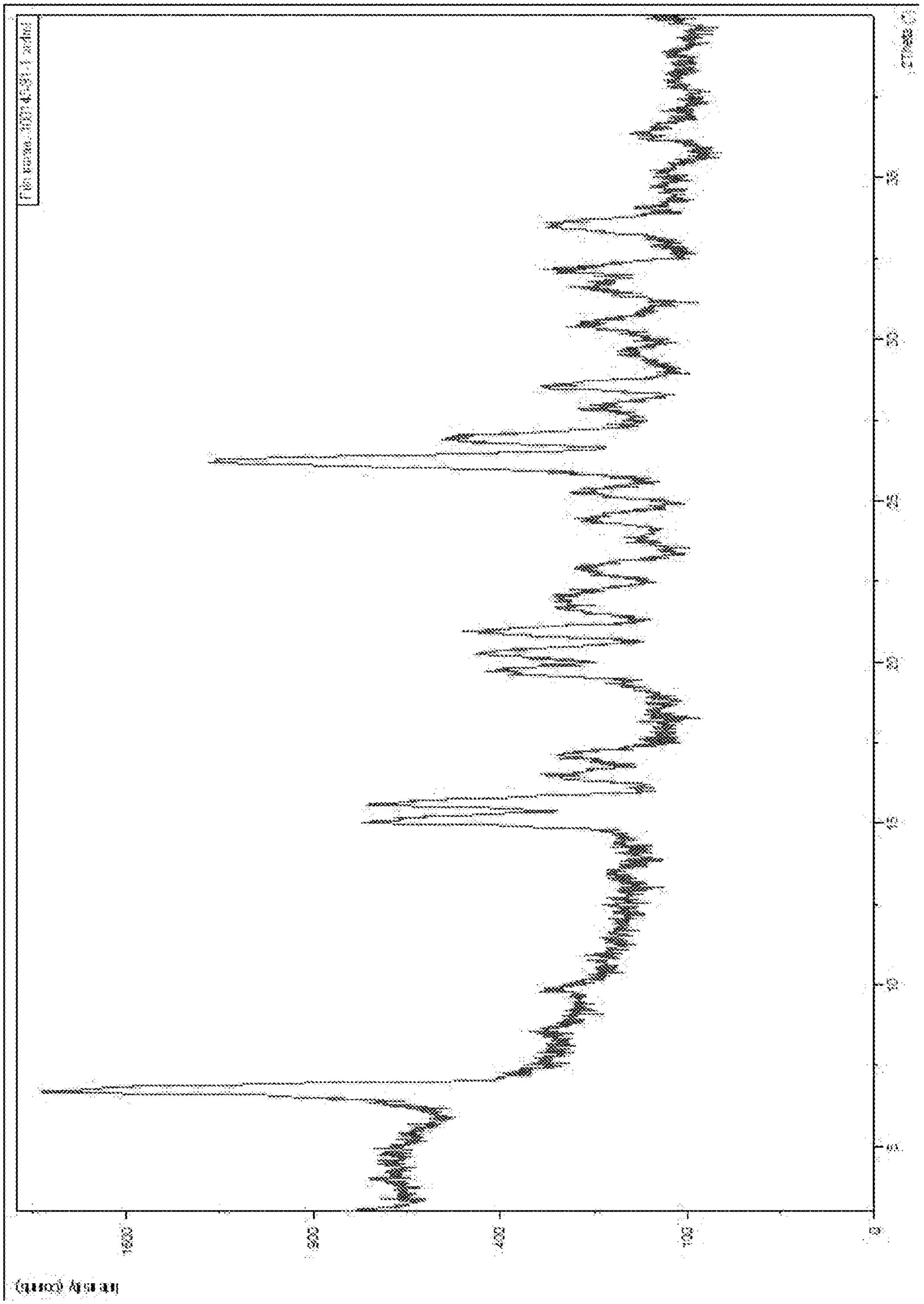
FIG. 2 shows an X-ray powder diffraction pattern (XRPD) for Form A.

In various embodiments, Form A can be characterized by an X-ray powder diffraction pattern, obtained as set forth in the Examples, having peaks at about 6.6, 14.9, 20.1, 21.4, and 26.8±0.2° 2θ using Cu Kα radiation. Form A optionally can be further characterized by an X-ray powder diffraction pattern having additional peaks at about 8.4, 24.2, 26.0, 33.3±0.2° 2θ using Cu Kα radiation. Form A optionally can be even further characterized by an X-ray powder diffraction pattern having additional peaks at about 6.2, 9.7, 13.2, 14.3, 15.4, 16.3, 16.9, 18.9, 19.5, 20.7, 21.8, 22.8, 23.6, 25.1, 27.3, 27.7, 28.4, 29.4, 30.2, 31.2, 31.5, 31.9, 33.9, 34.5, 34.9, 36.1, 36.8, 37.7, 38.5, and 39.7±0.2° 2θ using Cu Kα radiation. In various cases, Form A can be characterized by an XRPD pattern having peaks at about 6.2, 6.6, 8.4, 9.7, 13.2, 14.3, 14.9, 15.4, 16.3, 16.9, 18.9, 19.5, 20.1, 20.7, 21.4, 21.8, 22.8, 23.6, 24.3, 25.1, 26.0, 26.8, 27.3, 27.7, 28.4, 29.4, 30.2, 31.2, 31.5, 31.9, 33.3, 33.9, 34.5, 34.9, 36.1, 36.8, 37.7, 38.5, and 39.7±0.2° 2θ using Cu Kα radiation. In some embodiments, Form A has an X-ray powder diffraction pattern substantially as shown in FIG. 2, wherein by "substantially" is meant that the reported peaks can vary by about ±0.2°.It is well known in the field of XRPD that while relative peak heights in spectra are dependent on a number of factors, such as sample preparation and instrument geometry, peak positions are relatively insensitive to experimental details.

Figure 3:
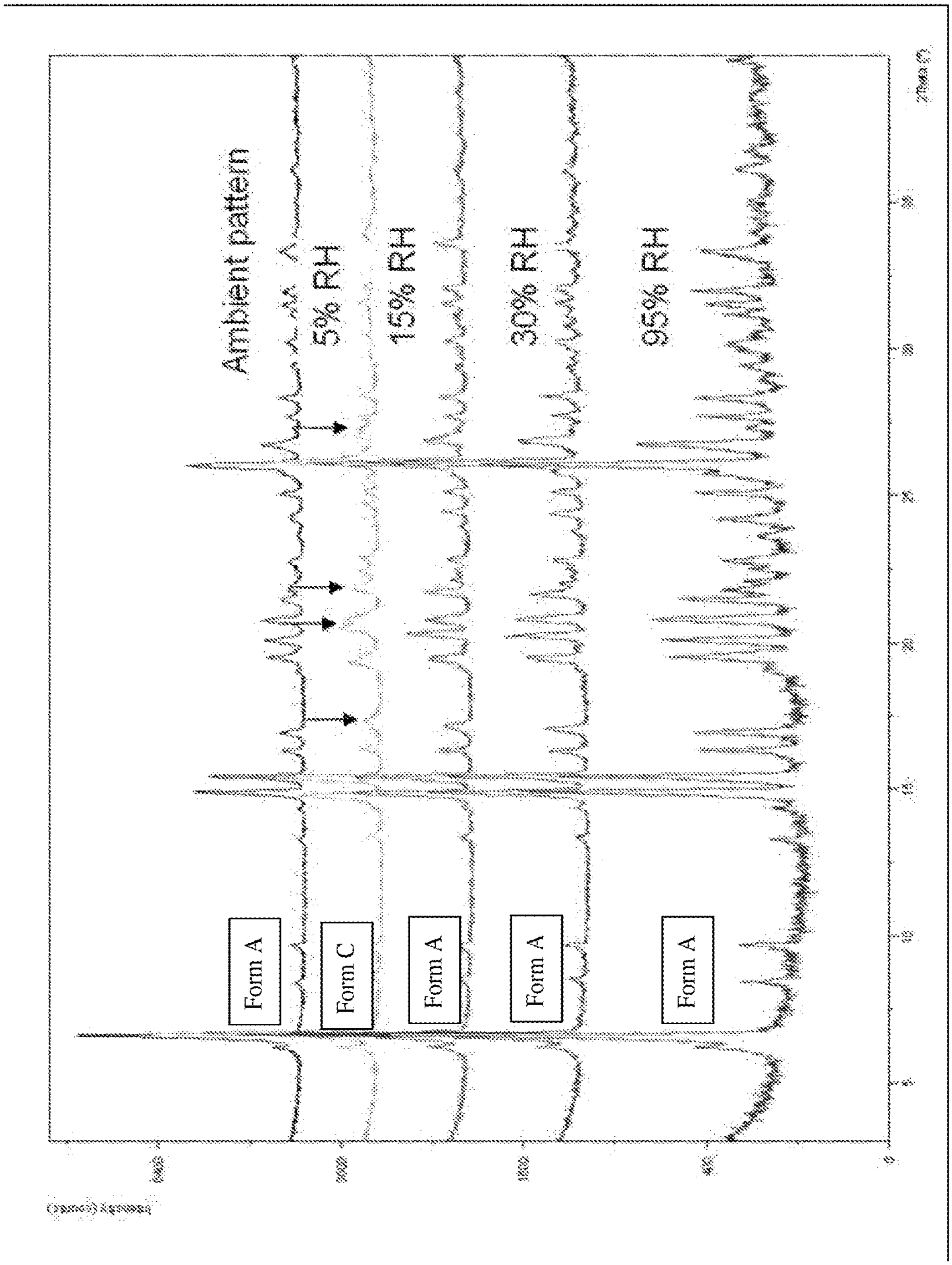
FIG. 3 shows an XRPD of a omecamtiv mecarbil dihydrochloride hydrate salt form at varying relative humidity conditions.
Figure 4:
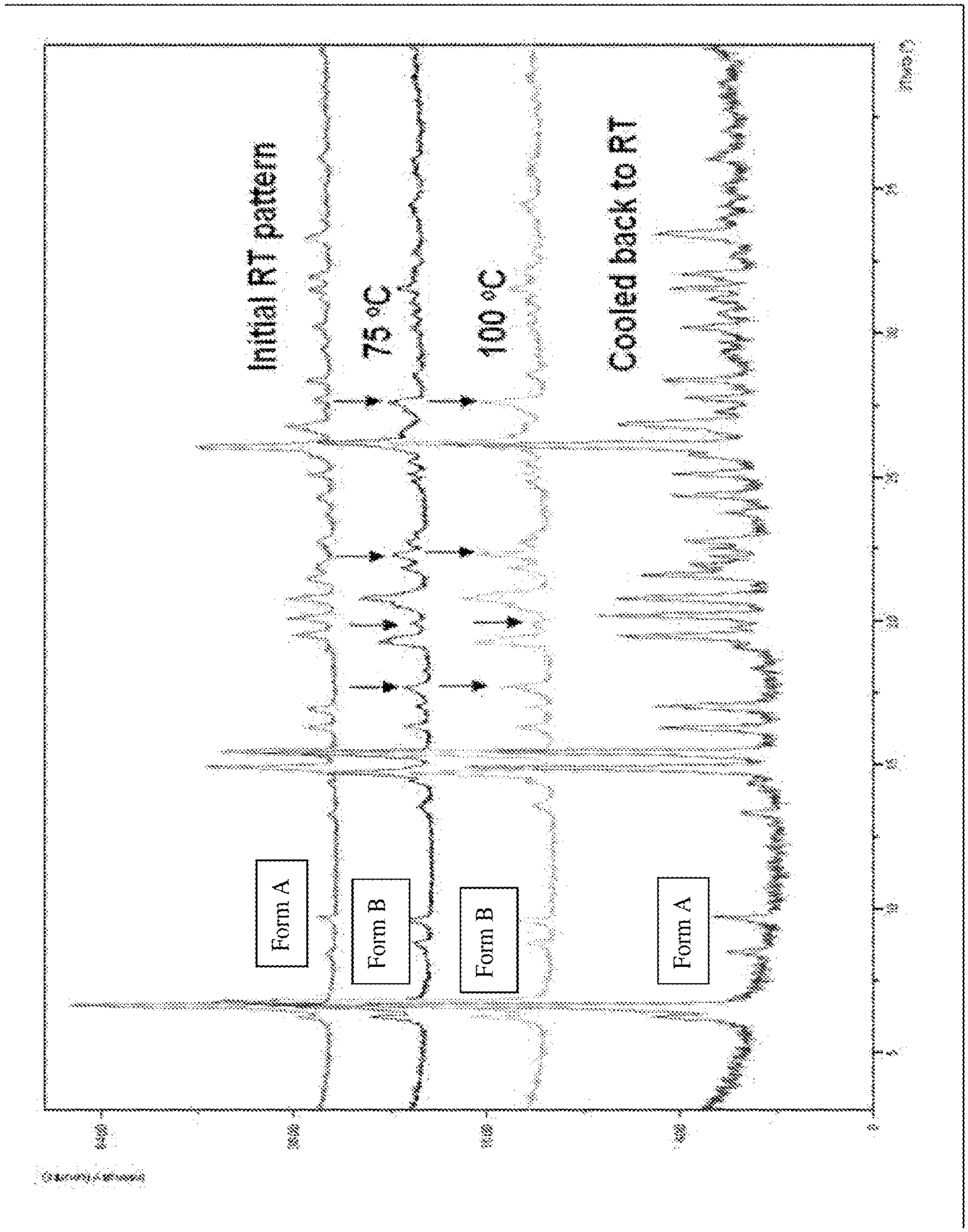
FIG. 4 shows an XRPD of a omecamtiv mecarbil dihydrochloride hydrate salt form at varying temperatures.
Figure 6:
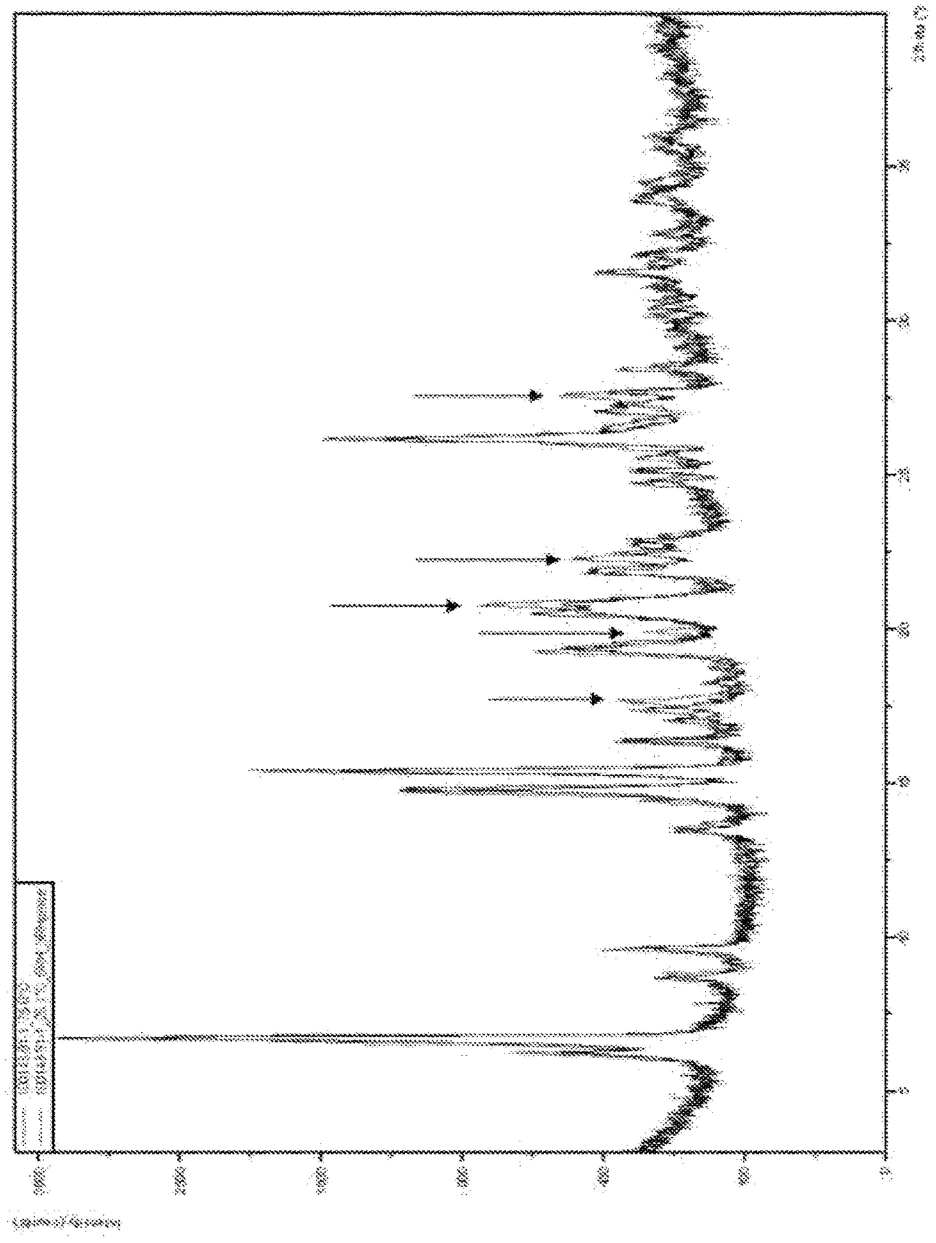
FIG. 6 shows an overlay of XRPD patterns for Forms A, B and C of omecamtiv mecarbil dihydrochloride salt.
Figure 7A:
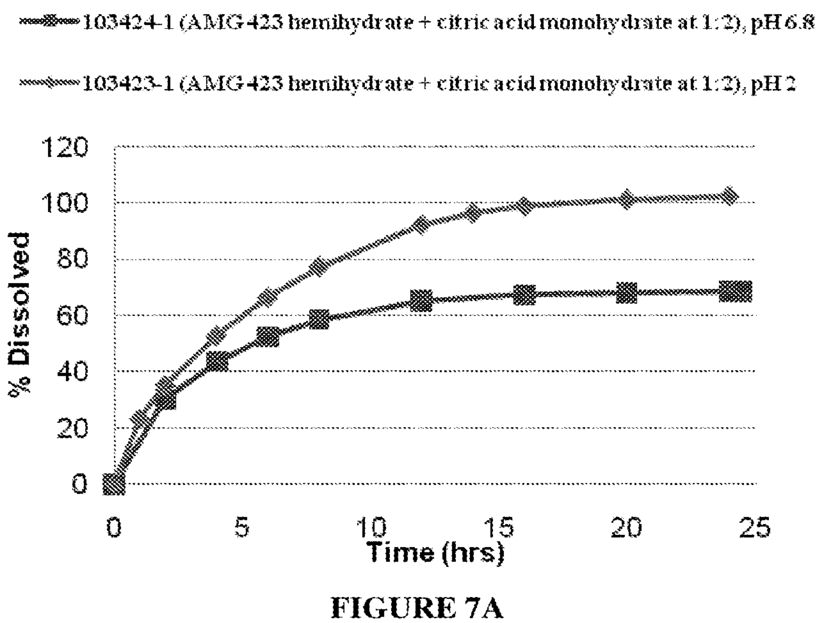
FIG. 7A shows drug release at two pHs (2 and 6.8) for a formulation of omecamtiv mecarbil free base hemihydrate.
Figure 7B:
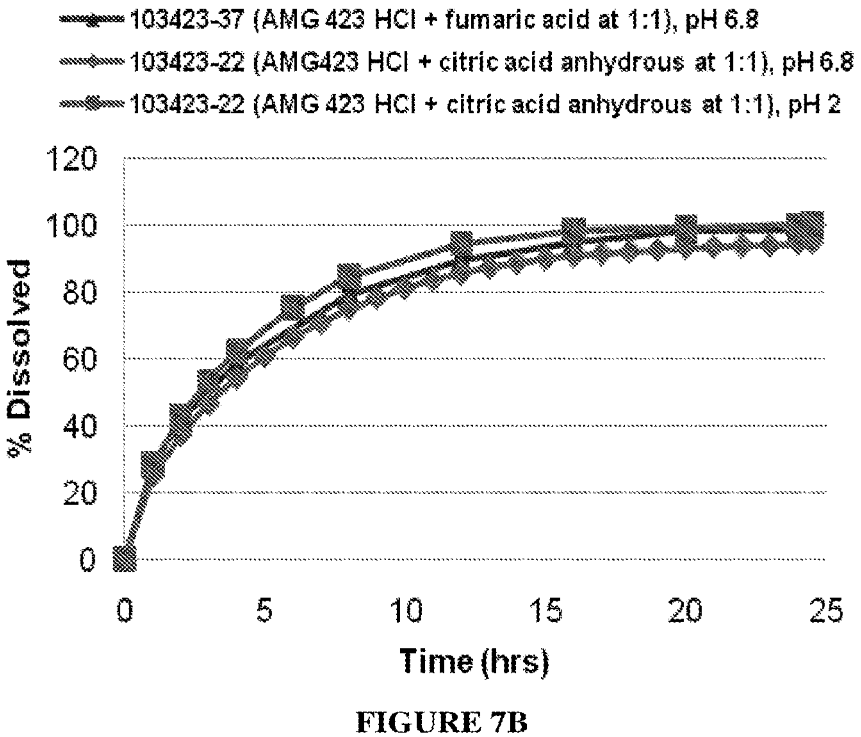
FIG. 7B shows drug release of two pHs (2 and 6.8) for a omecamtiv mecarbil dihydrochloride hydrate salt form, Form A.

Form B and Form C polymorphs of omecamtiv mecarbil, are metastable anhydrous dihydrochloride forms, and can be formed under varied hydration conditions, as noted in FIGS. 3, 4, and 6. Characteristic Form B 2-theta values include 6.8, 8.8, 14.7, 17.7, and 22.3±0.2° 2θ using Cu Kα radiation, and can additionally include peaks at 9.6, 13.5, 19.2, 26.2±0.2° 2θ using Cu Kα radiation. Form B can be characterized with XRPD pattern peaks at 6.2, 6.8, 8.8, 9.6, 13.5, 14.4, 14.7, 15.4, 16.3, 17.0, 17.7, 18.3, 19.2, 19.9, 20.5, 20.8, 21.8, 22.3, 22.7, 23.0, 24.8, 25.1, 25.5, 26.2, 26.4, 26.8, 27.5, 28.5, 30.2, 30.6, 31.1, 31.5, 32.1, 32.7, 34.1, 34.4, 35.5, 35.9, 38.1, 38.9±0.2° 2θ using Cu Kα radiation. Characteristic Form C 2-theta values include 6.7, 14.8, 17.4, 20.6, and 26.2±0.2° 2θ using Cu Kα radiation, and can additionally include peaks at 8.7, 22.0, 27.1, and 27.7±0.2° 2θ using Cu Kα radiation. Form C can be characterized with XRPD pattern peaks at 6.2, 6.7, 8.7, 9.6, 13.5, 14.5, 14.8, 15.4, 16.4, 17.1, 17.4, 18.4, 19.3, 19.5, 19.9, 20.6, 20.8, 21.8, 22.0, 22.5, 22.8, 24.3, 24.7, 25.1, 25.6, 26.2, 26.5, 27.1, 27.3, 27.7, 28.5, 30.0, 30.5, 31.0, 31.5, 32.2, 32.8, 34.1, 35.2, 36.0, 36.9, and 38.8±0.2° 2θ using Cu Kα radiation. In some embodiments, Forms B and C have an X-ray powder diffraction pattern substantially as shown in FIG. 6, wherein by "substantially" is meant that the reported peaks can vary by about ±0.2°.

In various embodiments, Form A can be characterized by a single crystal x-ray diffraction (XRD) pattern, obtained as set forth in the Examples section, wherein Form A comprises a triclinic space group of P-1 and unit cell parameters of about a=5.9979 (4) Å, b=13.4375 (9) Å, c=14.4250 (9) Å, α=97.617 (4)°; β=93.285 (4)°; and γ=94.585 (5)°. Form A optionally can be further characterized by the XRD parameters in the table, below.

| | |
|---|---|
| Wavelength | 1.54178 Å |
| Crystal system | Triclinic |
| Space group | P-1 |
| Unit cell dimensions | a = 5.9979(4) Å |
| | α = 97.617(4)° |
| | b = 13.4375(9) Å |
| | β = 93.285(4)° |
| | c = 14.4250(9) Å |
| | γ = 94.585(5)° |
| Volume | 1145.93(13) $Å^3$ |
| Z | 2 |
| Density (calculated) | 1.427 $Mg/m^3$ |
| Absorption coefficient | 2.945 $mm^{-1}$ |

Figure 5:
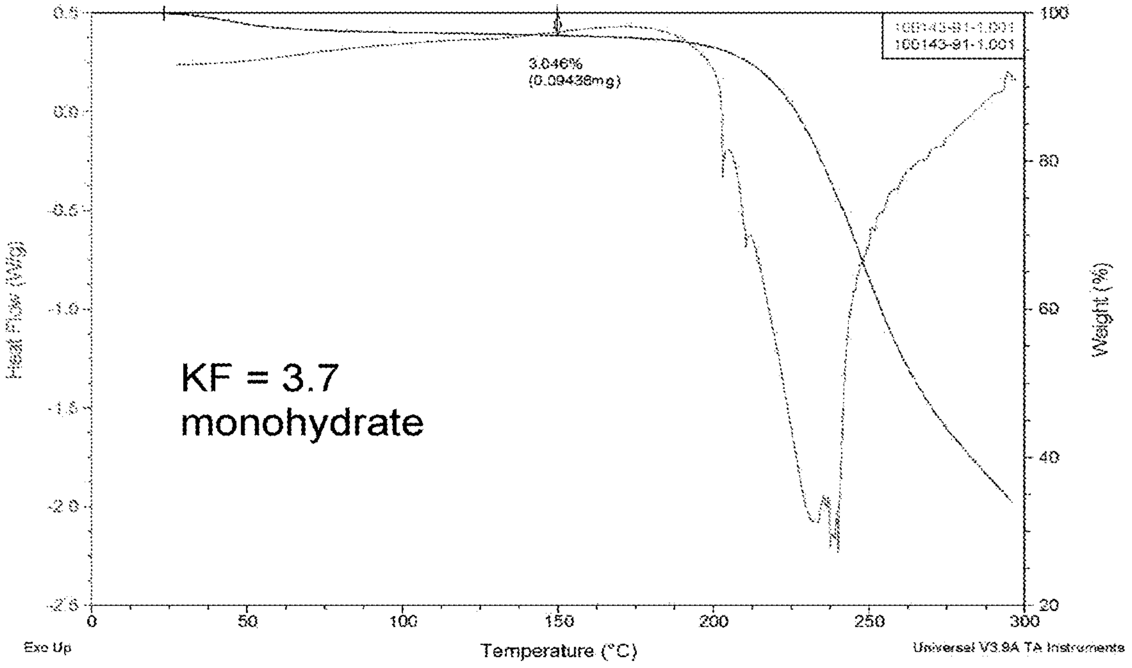
FIG. 5 shows the differential scanning calorimetry thermograph and thermogravimetric analysis for Form A.

DSC thermographs were obtained for Form A. The DSC curve indicates an endothermic transition that appears to be due to melting/decomposition around 235° C. Thus, in embodiments, Form A can be characterized by a DSC thermograph having a decomposition endotherm with an onset in a range of about 230° C. to about 240° C. when Form A in an open aluminum pan. For example, in embodiments wherein Form A is heated from about 25° C. at a rate of about 10° C./min, Form A can be characterized by a DSC thermograph having a decomposition endotherm with an onset of about 235° C., as shown in FIG. 5.

Form A also can be characterized by thermogravimetric analysis (TGA). Thus, Form A can be characterized by a weight loss in a range of about 2% to about 5% with an onset temperature in a range of about 100° C. to about 150° C. For example, Form A can be characterized by a weight loss of about 3%, up to 150° C. In some embodiments, Form A has a thermogravimetric analysis substantially as depicted in FIG. 5, wherein by "substantially" is meant that the reported TGA features can vary by about ±5° C. This weight loss was determined to be water via Karl Fischer (KF) analysis. KF analysis shows that the water content of Form A can be about 3.7, corresponding to a mono hydrate.

Form A can be characterized via variable temperature XRPD and variable relative humidity XRPD. The variable temperature XRPD data are shown in FIG. 4. The data indicate that when Form A hydrate is heated beyond the desolvation event shown in the TGA curve (about 75° C.), the material converts to a new dehydrated phase, Form B. When the material is cooled back down to ambient conditions, Form B resorbs water from the atmosphere and converts back to the hydrate Form A. The variable relative humidity XRPD data are shown in FIG. 3. The data indicate that when the hydrate Form A is exposed to 5% relative humidity, the material converts to a new dehydrated phase, Form C. When the material was exposed to 15% relative humidity and higher, Form C resorbs water from the environment and converts back to the hydrate Form A. These data are consistent with the vapor sorption experiment. An overlay of Form B and Form C are shown in FIG. 6. Arrows mark significant reflections of the two powder patterns indicating that the two phases are unique.

Also provided are compositions comprising a dihydrochloride hydrate form of omecamtiv mecarbil. In some embodiments, the compositions include at least about 50, about 60, about 70, about 80, about 90, about 95, about 96, about 97, about 98, or about 99% by weight of the dihydrochloride hydrate form of omecamtiv mecarbil. In some embodiments, the compositions include at least about 50, about 60, about 70, about 80, about 90, about 95, about 96, about 97, about 98, or about 99% by weight of Form A of the dihydrochloride hydrate form of omecamtiv mecarbil. In some embodiments, the compositions contain a mixture of two or more of Forms A, B, and C.

Also provided are pharmaceutical formulations comprising a dihydrochloride hydrate form of omecamtiv mecarbil and at least one pharmaceutically acceptable excipient. In some embodiments, the formulations include at least about 50, about 60, about 70, about 80, about 90, about 95, about 96, about 97, about 98, or about 99% by weight of the dihydrochloride hydrate form of omecamtiv mecarbil. In some embodiments, the formulations include at least about 50, about 60, about 70, about 80, about 90, about 95, about 96, about 97, about 98, or about 99% by weight of Form A of the dihydrochloride hydrate form of omecamtiv mecarbil. In some embodiments, the formulations contain a mixture of two or more of Forms A, B, and C.

Also provided is a method for the use of such pharmaceutical formulations for the treatment of heart failure, including but not limited to: acute (or decompensated) congestive heart failure, and chronic congestive heart failure; particularly diseases associated with systolic heart dysfunction.

Also provided is a synthesis of omecamtiv mecarbil comprising admixing methyl 4-(3-amino-2-fluorobenzyl)piperazine-1-caboxylate and phenyl (6-methylpyridin-3-yl) carbamate in the presence of a trialkylamine base to form omecamtiv mecarbil.

In some embodiments, the weight ratio of phenyl (6-methylpyridin-3-yl)carbamate hydrochloride (i.e., SM-2 or phenyl carbamate) to methyl 4-(3-amino-2-fluoro-benzyl) piperazine-1-carboxylate (i.e., SM-1 or piperazine nitro) is between about 1.1 and 1.5. In some embodiments, weight ratio of phenyl (6-methylpyridin-3-yl)carbamate hydrochloride to methyl 4-(3-amino-2-fluorobenzyl)piperazine-1-carboxylate is about 1.2.

In some embodiments, the admixing is conducted in the presence of an aprotic solvent. In some embodiments, the solvent is THF.

In some embodiments, the trialkylamine base is triethylamine, diisopropylethylamine, or a combination thereof. In some embodiments, the trialkylamine base comprises diisopropylethylamine.

In some embodiments, an excess of the trialkylamine base is used. In some embodiments, between about 1.1 and 1.5 equivalents of the trialkylamine base is used. In some embodiments, about 1.3 equivalents of the trialkylamine base is used.

In some embodiments, the admixing is conducted at 65° C.

In some embodiments, the method further comprises crystallizing the omecamtiv mecarbil in the presence of aqueous hydrochloric acid and an alcohol solvent to form omecamtiv mecarbil dihydrochloride hydrate.

In some embodiments, the alcohol solvent comprises isopropyl alcohol.

In some embodiments, the aqueous hydrochloric acid comprises 6N HCl.

In some embodiments, the method further comprises mixing the omecamtiv mecarbil dihydrochloride hydrate with at least pharmaceutically acceptable excipient to form a pharmaceutical formulation.

In some embodiments, the pharmaceutical formulation comprises omecamtiv mecarbil dihydrochloride hydrate; a sweller layer; and a semi-permeable membrane coating having at least one delivery port. The general properties of the drug layer and the sweller layer can be found in U.S. Pat. Pub. 2011/0182947, herein incorporated by reference.

In some embodiments, the pharmaceutical formulation is a modified release matrix tablet comprising omecamtiv mecarbil dihydrochloride hydrate; a control release agent; a pH modifying agent; a filler; and a lubricant.

In some embodiments, the methyl 4-(3-amino-2-fluorobenzyl)piperazine-1-caboxylate is prepared by a process comprising: hydrogenating methyl 4-(2-fluoro-3-nitrobenzyl) piperazine-1-carboxylate in the presence of a hydrogenation catalyst to form methyl 4-(3-amino-2-fluorobenzyl) piperazine-1-caboxylate.

In some embodiments, the hydrogenation catalyst comprises palladium. In some embodiments, the hydrogenation catalyst is palladium on carbon.

Also provided is a method of preparing omecamtiv mecarbil dihydrochloride hydrate comprising crystallizing omecamtiv mecarbil in the presence of aqueous hydrochloric acid and an alcohol solvent to form omecamtiv mecarbil dihydrochloride hydrate.

In some embodiments, the alcohol solvent comprises isopropyl alcohol.

Also provided is a method of preparing omecamtiv mecarbil dihydrochloride hydrate comprising:

(a) hydrogenating methyl 4-(2-fluoro-3-nitrobenzyl)piperazine-1-carboxylate in the presence of a hydrogenation catalyst to form methyl 4-(3-amino-2-fluorobenzyl)piperazine-1-caboxylate;

(b) admixing methyl 4-(3-amino-2-fluorobenzyl)piperazine-1-caboxylate and phenyl (6-methylpyridin-3-yl)carbamate in the presence of a trialkylamine base to form omecamtiv mecarbil as a free base; and (c) crystallizing the omecamtiv mecarbil free base in the presence of aqueous hydrochloric acid and an alcohol solvent to form omecamtiv mecarbil dihydrochloride hydrate salt.

This synthesis provides high overall yields (greater than 70%). In addition, the dihydrochloride salt that results from the steps, can be formed as long rods when crystallized, having improved bulk properties, filtration times of minutes (compared to days for the free base form) and is highly soluble (greater than 40 mg/mL at pH 3.8). In various cases, the resulting salt is the dihydrochloride hydrate Form A.

EXAMPLES

General Methods

Reagents and solvents were used as received from commercial sources. $^1H$ NMR spectra were recorded on a 400 MHz spectrometer. Chemical shifts are reported in ppm from tetramethylsilane with the solvent resonance as the internal standard ($CDCl_3$, DMSO-$d_6$). Data are reported as follows: chemical shift, multiplicity (s=singlet, d=doublet, t=triplet, q=quartet, br=broad, m=multiplet), coupling constants (Hz) and integration. $^{13}C$ NMR spectra were recorded on a 100 MHz spectrometer with complete proton decoupling. Chemical shifts are reported in ppm from tetramethylsilane with the solvent as the internal reference ($CDCl_3$, DMSO-$d_6$). All solvent charges are made with respect to starting 2-Fluoro-3-nitrotoluene.

X-ray powder diffraction data was obtained using the Phillips x-ray automated powder diffractometer (X'Pert) that was equipped with a fixed slit. The radiation was CuKα (1.541837 Å) and the voltage and current were 45 kV and 40 mA, respectively. Data was collected at room temperature from 3.000 to 40.009 degree 2-theta; step size was 0.008 degrees; counting time was 15.240 seconds. Samples ranging from 5-40 mg were prepared on the sample holder and the stage was rotated at a revolution time of 2.000 seconds.

The thermal properties of omecamtiv mecarbil bis-HCl salt were characterized using a DSC Q1000 or DSC Q 100 model, TA Instruments, differential scanning calorimetry, and a Q 500, TA Instruments, thermogravimetric analyzer. Data analysis was performed utilizing Universal Analysis 2000, TA Instruments. Heating rates of 10° C./min were used over a variety of temperature ranges for differential scanning calorimetry and thermogravimetric analysis. Samples ranging from <1-5 mg were prepared in crimped, hermetic or open aluminum pans for DSC analysis.

Moisture balance data was collected using a VTI SGA 100 symmetrical vapor sorption analyzer. Relative humidity was varied in increments of 5%, between 5% and 95% relative humidity during the adsorption run, and from 95% to 5% relative humidity during the desorption run. Equilibrium criteria was set at 0.01% weight change in 1 minute with a max equilibrium time of 180 minutes. Approximately 1-15 mg of sample was used.

A colorless blade of $C_{20}H_{28}C_{12}FN_5O_4$, approximate dimensions 0.03 mm×0.12 mm×0.50 mm, was used for the X-ray crystallographic analysis. The X-ray intensity data were measured at 100(2) K on a Bruker Kappa APEX II system equipped with a graphite monochromator and a CuKα fine-focus sealed tube (λ=1.54178 Å) operated at 1.2 kW power (40 kV, 30 mA). The detector was placed at a distance of 5.0 cm. from the crystal.

A total of 7824 frames were collected with a scan width of 0.5° in ω and φ and an exposure time of 90 sec/frame. The total data collection time was 260 hours. The frames were integrated with the Bruker SAINT software package using a narrow-frame integration algorithm. The integration of the data using a Triclinic cell yielded a total of 12349 reflections to a maximum θ angle of 69.57° (0.83 Å resolution), of which 4046 were independent (redundancy 3.06), completeness=93.6%, $R_{int}$=5.13%, $R_{sig}$=5.18%) and 3351 (82.8%) were greater than >2sigma (I)σ ($F^2$). The final cell constants of a=5.9979 (4)Å, b=13.4375(9)Å, c=14.4250(9)Å, α=97.617(4)°, β=93.285(4)°, γ=94.585(5)°, volume=1145.95(13)$Å^3$, are based upon the refinement of the XYZ-centroids of 4790 reflections above 20 σ(I) with 6.196°<2θ<138.239°. Analysis of the data showed negligible decay during data collection. Data were corrected for absorption effects using the multiscan technique (SADABS). The ratio of minimum to maximum apparent transmission was 0.350. The calculated minimum and maximum transmission coefficients (based on crystal size) are 0.3206 and 0.9168.

The structure was solved and refined using the Bruker SHELXTL (Version 6.1) Software Package, using the space group P-1, with Z=2 for the formula unit, $C_{20}H_{28}Cl_2FN_5O_4$. The final anisotropic full-matrix least-squares refinement on $F^2$ with 320 variables converged at R1=6.43%, for the observed data and wR2=19.18% for all data. The goodness-of-fit was 1.067. The largest peak on the final difference electron density synthesis was 1.084 $e^-/Å^3$ and the largest hole was −0.527 $e^-/Å^3$ with an RMS deviation of 0.101 $e^-/Å^3$ On the basis of the final model, the calculated density was 1.427 g/$cm^3$ and F(000), 516 $e^-$.

Two positions for partial water occupancies were found and refined in this structure. The occupancies of the waters were refined independently to 53% and 41% for a total water content of 0.94 equivalents of water per omecamtiv mecarbil molecule. This is consistent with other measures of water content in this form of this compound. Hydrogen atoms on one of the solvating waters, the one with an occupancy of 41%, were found in the electron density difference map and refined with bond lengths fixed at 1.01 Å. The hydrogen atoms on N3, C4 and N4 were found and allowed to refine isotropically. All other hydrogen atoms were placed at idealized positions and refined riding mode.

X-Ray powder diffraction data (XRPD) were obtained using a PANalytical X'Pert PRO diffractometer (PANalytical, Almelo, The Netherlands) fitted with a real time multiple strip (RTMS) detector. The radiation used was CuKα (1.54 Å) and the voltage and current were set at 45 kV and 40 mA, respectively. Data were collected at room temperature from 5 to 45 degrees 2-theta with a step size of 0.0334 degrees. Samples were prepared on a low background sample holder and placed on the sample stage which was rotated with a 2 second revolution time.

Alternatively, XRPD data were obtained using a PANalytical X'Pert PRO diffractometer (PANalytical, Almelo, The Netherlands) fitted with a RTMS detector. The radiation used was CuKα (1.54 Å) and the voltage and current were set at 45 kV and 40 mA, respectively. Data were collected at room temperature from 5 to 40, degrees 2-theta with a step size of either 0.0334 degrees. Samples were prepared on a low background sample holder and placed on the sample stage which was rotated with a 2 second revolution time.

Alternatively, XRPD data were obtained using a PANalytical X'Pert PRO diffractometer (PANalytical, Almelo, The Netherlands) fitted with a RTMS detector. The radiation used was CuKα (1.54 Å) and the voltage and current were set at 45 kV and 40 mA, respectively. Data were collected at room temperature from 5 to 40, degrees 2-theta with a step size of either 0.0167 degrees. Samples were prepared on a low background sample holder and placed on the sample stage which was rotated with a 2 second revolution time.

Alternatively, XRPD data were obtained using a PANalytical X'Pert Pro diffractometer (PANalytical, Almelo, The Netherlands) fitted with a RTMS detector. The radiation used was CuKα (1.54 Å) and the voltage and current were set at 45 kV and 40 mA, respectively. Data were collected at room temperature from 3 to 40, degrees 2-theta with a step size of 0.008 degrees. Samples were prepared on a low background sample holder and placed on the sample stage with a 2 second revolution time.

Alternatively, XRPD data were obtained using a Bruker D8 Discover X-ray diffraction system (Bruker, Billerica, MA) fitted with a motorized xyz sample stage and a GADDS area detector. The radiation used was CuKα (1.54 Å) and the voltage and current were set at 45 kV and 40 mA, respectively. The solid samples on a flat glass plate were mapped and for each sample an area of 1 $mm^2$ was scanned in an oscillating mode for 3 minutes from 5 to 48 degrees 2-theta.

Differential Scanning Calorimetry (DSC) data was collected using standard DSC mode (DSC Q200, TA Instruments, New Castle, DE). A heating rate of 10° C./min was employed over a temperature range from 40° C. to 300° C. Analysis was run under nitrogen and samples were loaded in standard, hermetically-sealed aluminum pans. Indium was used as a calibration standard.

Alternatively, DSC data were collected using temperature-modulated DSC mode (DSC Q200, TA Instruments, New Castle, DE). After sample equilibration at 20° C. for five minutes, the heating rate of 3° C./min was employed with a modulation of +/−0.75° C./min over a temperature range from 20° C. to 200° C. Analysis was run under nitrogen and samples were loaded in standard, uncrimped aluminum pans. Indium was used as a calibration standard.

Manufacture of Omecamtiv Mecarbil Dihydrochloride Hydrate Synthetic Route to Omecamtiv Mecarbil

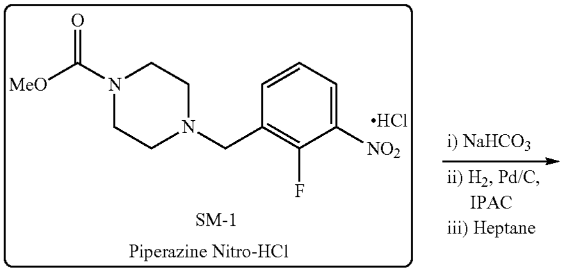

SM-1
Piperazine Nitro-HCl

-continued

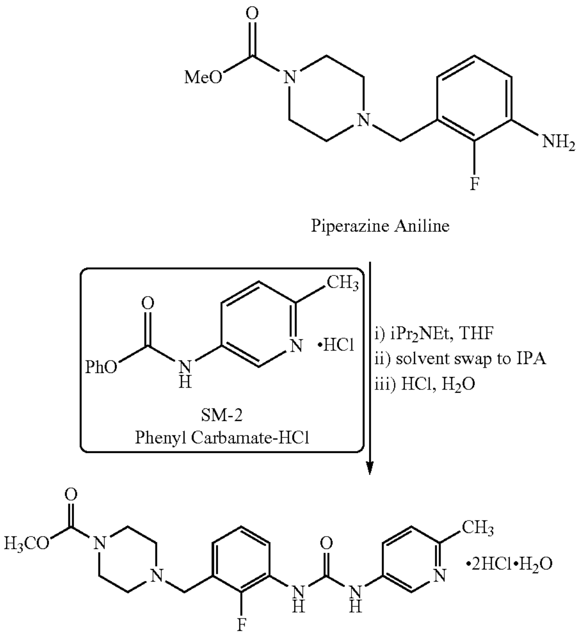

Piperazine Aniline

SM-2
Phenyl Carbamate-HCl omecamtiv mecarbil-2HCl—$H_2O$

Synthesis of the API SM Piperazine Nitro-HCl

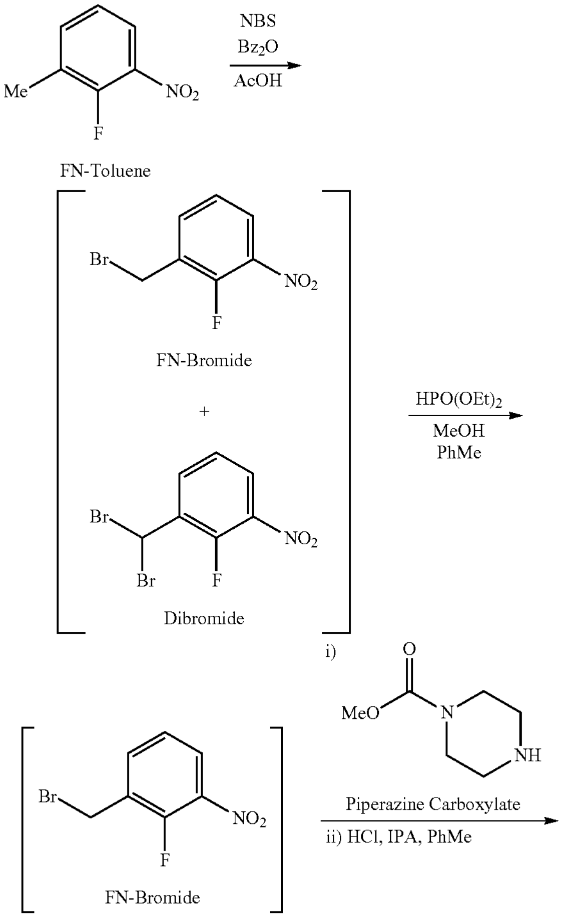

FN-Toluene

FN-Bromide

+

Dibromide

Piperazine Carboxylate

FN-Bromide

-continued

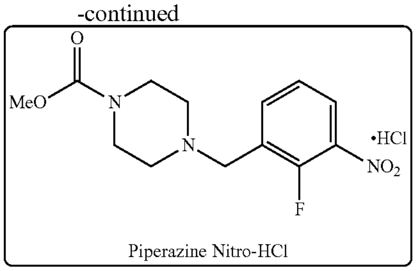

Piperazine Nitro-HCl

88% overall

In a 60 L reactor (containing no exposed Stainless steel, Hastelloy®, or other metal parts) equipped with a reflux/return condenser and scrubber charged with a 5N NaOH solution, a mechanically stirred mixture of FN-Toluene (2.0 kg, 12.89 mol, 1.0 equiv.), N-Bromosuccinimide (3.9 kg, 21.92 mol, 1.70 equiv.), benzoyl peroxide (125.0 g, 0.03 equiv., 0.39 mol, containing 25 wt % water), and acetic acid (7.0 L, 3.5 volumes) was heated to 85° C. under an atmosphere of nitrogen for 7 hours. A solution of $H_3PO_3$ (106.0 g, 1.29 mol, 0.1 equiv.) and acetic acid (200 mL, 0.1 volume), prepared in separate vessel, was added. The reaction mixture was agitated for 0.5 h and analysis of an aliquot confirmed complete decomposition of benzoyl peroxide (not detected, $HPLC_{254\ nm}$). The reaction mixture was cooled to 22° C. DI Water (8.0 L, 4 volumes) and toluene (16.0 L, 8 volumes) were charged, the biphasic mixture was agitated (20 min), and the layers were separated. Aqueous 1.6N NaOH (14.0 L, 7.0 volumes) was added to the organic layer at a rate allowing the batch temperature to stay under 25° C. and the pH of the resultant aqueous phase was measured (≥11). The biphasic mixture was filtered through a 5 μm Teflon® cartridge line and the layers were separated. The filter line was washed with another 2 L of toluene.

The assay yields were 2.5% of FN-Toluene, 62.3% of FN-Bromide and 30.0% of Di-Bromide. The toluene solution contained no benzoyl peroxide, succinimide, or α-bromoacetic acid and water content by KF titration was 1030 ppm (This solution could be held under nitrogen at room temperature for >12 h without any change in the assay yield).

To this solution at room temperature was added diisopropylethylamine (880.0 g, 6.63 mol, 0.53 equiv.) followed by methanol (460 mL, 11.28 mol, 0.88 equiv.) and heated to 40° C. A solution of diethylphosphite (820.0 g, 5.63 mol, 0.46 equiv.) in methanol (460 mL, 11.28 mol, 0.88 equiv.) was prepared and added to the reaction mixture at 40° C. through an addition funnel over a period of 1 hour at such a rate that the batch temperature was within 40±5° C. The contents were stirred for a period of 3 h at 40° C. from the start of addition and cooled to room temperature and held under nitrogen atmosphere for 12 hours. The assay yield of the reaction mixture was 2.5% FN-Toluene 92.0% FN-Bromide and 0.2% Di-Bromide. This solution is used as such for the alkylation step.

Characterization for components of final product mixture (collected for pure compounds).

2-Fluoro-3-Nitrotoluene (FN-Toluene): $^1H$ NMR (400 MHZ, CHLOROFORM-d) δ ppm 2.37 (s, 1H), 7.13-7.20 (m, 1H), 7.45-7.51 (m, 1H), 7.79-7.85 (m, 1H). $^{13}C$ NMR (100 MHz, CHLOROFORM-d) δ ppm 14.3 (d, J=5 Hz), 123.3 (d, J=3 Hz), 123.6 (d, J=5 Hz), 128.2 (d, J=16 Hz), 136.7 (d, J=5 Hz), 137.5 (broad), 153.7 (d, J=261 Hz); 1-(bromomethyl)-2-fluoro-3-nitrobenzene (FN-Bromide):

1H NMR (400 MHz, CHLOROFORM-d) δ ppm 4.56 (s, 1H), 7.28-7.34 (m, 1H), 7.69-7.76 (m, 1H), 7.98-8.05 (m, 1H). $^{13}$C NMR (100 MHZ, CHLOROFORM-d) δ ppm 23.6 (d, J=5 Hz), 124.5 (d, J=5 Hz), 126.1 (d, J=3 Hz), 128.5 (d, J=14 Hz), 136.5 (d, J=4 Hz), 137.7 (broad), 153.3 (d, J=265 Hz). DSC: single melt at 53.59° C. Exact Mass $[C_7H_5BrFNO_2+H]^+$: calc.=233.9566, measured=233.9561; 1-(dibromomethyl)-2-fluoro-3-nitrobenzene (Dibromide): $^1$H NMR (400 MHz, CHLOROFORM-d) δ ppm 6.97 (s, 1H), 7.39-7.45 (m, 1H), 8.03-8.10 (m, 1H), 8.16-8.21 (m, 1H). $^{13}$C NMR (100 MHz, CHLOROFORM-d) δ ppm 29.2 (d, J=7 Hz), 124.9 (d, J=5 Hz), 127.1 (d, J=2 Hz), 132.1 (d, J=11 Hz), 135.7 (d, J=2 Hz), 137.2 (broad), 149.8 (d, J=266 Hz). DSC: single melt at 49.03° C. Exact Mass $[C_7H_4Br_2FNO_2+H]^+$: calc.=311.8671, measured=311.8666.

Piperazine Nitro-HCl:

To a mechanically stirred toluene solution (9 volumes) of FN-Bromide (prepared from previous step) in a 60 L reactor at 22° C. under an atmosphere of nitrogen, diisopropylethylamine was charged (1.90 kg, 14.69 mol, 1.14 equiv.). To this mixture a solution of piperazine carboxylate methylester (Piperazine Carboxylate) (2.03 kg, 14.05 mol, 1.09 equiv.) in toluene (1.0 L, 0.5 volumes) was added at a rate allowing the batch temperature to stay under 30.0° C. (Exothermic. During the addition, jacket temperature was adjusted to 5° C. in order to maintain batch temperature below 30° C. The mixture was agitated at 22° C. for 3 hours and analysis of an aliquot confirmed completion of the alkylation reaction (<1.0 LCAP FN-Bromide, $HPLC_{254\ nm}$). The reaction mixture was treated with aqueous $NH_4Cl$ (20 wt %, 10.0 L, 5 volumes; prepared from 2.0 kg of $NH_4Cl$ and 10.0 L of DI water), the biphasic mixture was agitated (30 min), and the layers were separated. The organic layer was sequentially washed with aqueous $NaHCO_3$ (9 wt %, 10.0 L, 5 volumes; prepared from 0.90 kg of $NaHCO_3$ and 10.0 L of DI water). The organic layer was filtered through a 5 μm Teflon® cartridge line and transferred in a drum, washed the filter line with another 1.0 L toluene and the combined toluene solution (10.0 volumes) weighed, and assayed (HPLC) to quantify Piperazine Nitro free base. The assay yield for the Piperazine Nitro-freebase is 89.0%, FN-Toluene 2.5% and FN-Bromide 0.2% with FN-Bromide undetected. The total loss of product to the aqueous washes is <1.0%. This solution under nitrogen atmosphere is stable for more than 12 h.

To a mechanically stirred toluene solution of Piperazine Nitro free base, prepared as described above, at 22° C. in a 60 L reactor under an atmosphere of nitrogen, IPA (19.4 L, 9.7 volumes) and DI water (1.0 L, 0.5 volume) were charged. The mixture was heated to 55° C. and 20% of the 1.4 equiv. of conc. HCl (Titrated prior to use and charge based on titer value; 276.0 mL, 3.21 mol) was charged. The contents were agitated for 15 min and Piperazine Nitro-HCl seed (130.0 g, 0.39 mol, 0.03 equiv.) was charged as slurry in IPA (400 mL, 0.2 volume). The mixture was agitated for 30 min and the remaining conc. HCl (80% of the charge, 1.10 L, 12.82 mol) was added over a period of 4 hours. The mixture was stirred at 55° C. for 1 h, cooled to 20° C. in a linear manner over 1.5 hours, and agitated at this temperature for 12 hours. The supernatant concentration of Piperazine Nitro-HCl was measured (2.8 mg/g). The mixture was filtered through an aurora filter equipped with a 5 μm Teflon® cloth. The mother liquor were transferred to a clean drum and assayed. The filter cake was washed twice with IPA (11.2 L, 5.6 volumes) and dried to constant weight (defined as ≤1.0% weight loss for 2 consecutive TGA measurements over a period of 2 hours) on filter with vacuum and a nitrogen sweep (14 h). The combined losses of Piperazine Nitro-HCl in the mother liquors and the washes were 2.5%. Piperazine Nitro-HCl was isolated 3.59 kg in 87.6% corrected yield with >99.5 wt % and 99.0% LCAP purity.

Methyl 4-(2-fluoro-3-nitrobenzyl)piperazine-1-carboxylate hydrochloride (Piperazine Nitro-HCl): $^1$H NMR (300 MHz, DMSO-d) δ ppm 3.25 (br. s, 3H), 3.52-3.66 (m, 8H), 4.47 (s, 2H), 7.44-7.63 (t, 1 H, J=8 Hz), 7.98-8.15 (m, 1H), 8.17-8.34 (m, 1H). $^{13}$C NMR (75 MHz, DMSO-d) δ ppm 50.3, 51.4, 52.8, 119.6 (d, J=14 Hz), 125.1 (d, J=5 Hz), 127.9, 137.4 (d, J=8 Hz), 139.8 (d, J=3 Hz), 152.2, 154.7, 155.7. DSC: melt onset at 248.4° C. Exact Mass $[C_{13}H_{16}FN_3O_4+H]^+$: calculated=298.1203, measured=298.1198.

Alternative Processes for the Synthesis of Piperazine Nitro:

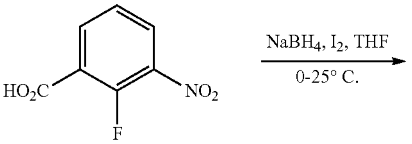

1
2-fluoro-3-nitrobenzoic acid

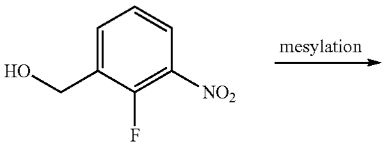

2
(2-fluoro-3-nitrophenyl) methanol

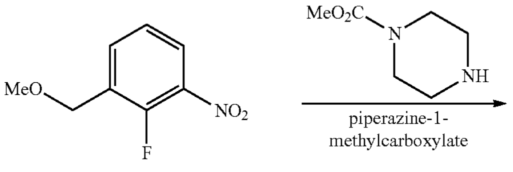

2
2-fluoro-3-nitrobenzyl methanesulfonate

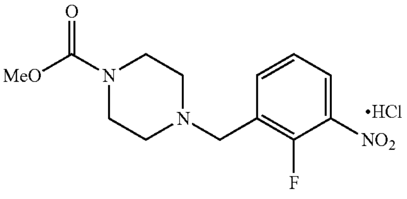

PC11SM3031
methyl 4-(2-fluoro-3-nitrobenzyl)piperazine-1-carboxylate hydrochloride A mixture of $NaBH_4$ (1.7 g, 44 mmol) in THF (68 mL) was treated 2-fluoro-3-nitrobenzoic acid (3.4 g, 18.4 mmol) and cooled to 0-5° C. A solution of iodine (4.7 g, 18.4 mmol) in THF (12 mL) was then added drop wise at a rate to control off-gassing. The progress of the reaction was assessed by HPLC. After 2 hours HPLC assay indicated 4% AUC of 2-fluoro-3-nitrobenzoic acid remained. The mixture was quenched into 1 M HCl (30 mL) and extracted with MTBE (5 mL). The organics were then washed with 20% aqueous KOH solution and 10% sodium thiosulfate. The organics were dried with $Na_2SO_4$, filtered over Celite and concentrated to afford (2-fluoro-3-nitrophenyl)methanol (2.8 g, 88%, 89% AUC by HPLC).

A solution of (2-fluoro-3-nitrophenyl)methanol (2.8 g, 16 mmol) in 2-MeTHF (26 mL) was treated with triethylamine (4.5 mL, 32 mmol) and cooled to 0-5° C. The solution was then treated with methanesulfonyl chloride (1.6 mL, 21 mmol). The progress of the reaction was assessed by HPLC. After 30 minutes at 0-5° C., the reaction was deemed complete. The mixture was quenched with water (14 mL) and the phases were separated. The organics were washed with brine, dried with $Na_2SO_4$, filtered over Celite and concentrated to afford 2-fluoro-3-nitrobenzyl methanesulfonate (3.3 g, 83.1%, 81% AUC by HPLC) as a yellow oil.

A solution of 2-fluoro-3-nitrobenzyl methanesulfonate (3.3 g, 13 mmol, AMRI lot # 46DAT067B) in toluene (33 mL), was treated with diisopropylethylamine (2.7 mL, 15 mmol) in one portion. A solution of methylpiperazine-1-carboxylate (2.1 g, 15 mmol) in toluene (1.1 mL) was added slowly via syringe to maintain between 23-29° C. The reaction was stirred for 16 hours following the addition. An HPLC assay after this time showed that the reaction was complete. 20% Aqueous $NH_4Cl$ (11 mL) was added at 20-25° C. The biphasic mixture was stirred for 15 minutes, and the phases were separated. This process was repeated using 9% aqueous sodium bicarbonate (11 mL). The toluene layer was then filtered over Celite at 20-25° C. 2-propanol (50 mL) and water (1.1 mL) were added to the toluene solution and the mixture heated to 55-60° C. The mixture was then treated with 37 wt % HCl (1.6 mL, 18.7 mmol) over 20 minutes. A precipitate was noted following the addition. When the addition was complete, the mixture was allowed to cool gradually to 20-25° C. and was stirred for hours before filtering and washing with IPA (2 bed volumes).

The cake was then dried at under vacuum to afford 4-(2-fluoro-3-nitrobenzyl)piperazine-1-carboxylate hydrochloride (2.41 g, 54%, 90% AUC by HPLC, 88 wt % by HPLC).

Piperazine Nitro Freebase:

In a 60 L reactor equipped with a reflux/return condenser, a mixture of Piperazine Nitro-HCl (2.0 kg, 5.99 mol, 1.0 equiv.) and isopropyl acetate (6.0 L, 3.0 volumes) was mechanically agitated at ambient temperature under an atmosphere of nitrogen. A solution of sodium bicarbonate (629 g, 7.49 mol, 1.25 equiv.) and water (7.5 L, 3.75 volume), prepared in separate vessel, was added. The biphasic mixture was agitated (15 min), and the layers were separated. The upper organic layer (containing product) was transferred to a separate vessel while the reactor was rinsed with water and isopropanol. The organic layer was then transferred through an inline 5 μm Teflon® cartridge back into the clean 60 L reactor. The filter line was washed with 4.0 L (2.0 volumes) of isopropanol into the 60 L reactor. An additional 12.0 L (6.0 volumes) of isoproponal was added to the 60 L reactor and heated to 40° C. Under reduced pressure (50 torr) the batch was concentrated down to approximately 6 L (3.0 volumes). The solution was cooled from 27° C. to 20° C. in a linear manner over 10 minutes. Water (4.0 L, 2.0 volumes) was added at 20° C. over 30 minutes followed by Piperazine Nitro Freebase seed (18 g, 0.06 mol, 0.01 equiv). The mixture was aged for 5 minutes and the remaining water (24.0 L, 12.0 volumes) was added over 90 minutes. After holding overnight at 20° C., the supernatant concentration of Piperazine Nitro Freebase was measured (<10 mg/mL). The mixture was filtered through an aurora filter equipped with a 12 μm Teflon® cloth. The filter cake was washed with a mixture of water (3.3 L, 1.65 volumes) and isopropanol (700 mL, 0.35 volumes) and dried to constant weight (defined as ≤1.0% weight loss for 2 consecutive TGA measurements over a period of 2 hours) on filter with vacuum and a nitrogen sweep (48 h). The combined losses of Piperazine Nitro Freebase in the mother liquors and the wash were aproximately 7.5%. Piperazine Nitro Freebase was isolated 1.67 kg in 92.5% corrected yield with 100.0 wt % and 99.4% LCAP purity.

Synthesis of the API SM Phenyl Carbamate-HCl

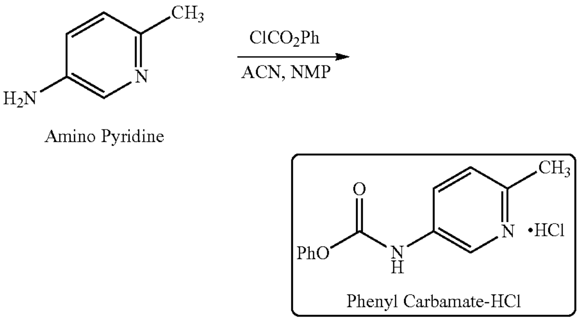

Amino Pyridine

Phenyl Carbamate-HCl

A 60 L, glass-lined, jacketed reactor set at 20° C. under nitrogen atmosphere and vented through a scrubber (containing 5N NaOH) was charged with 2.5 kg of Amino Pyridine (1.0 equiv, 23.1 moles), followed by 25 L (19.6 kg, 10 vol) acetonitrile. After initiating agitation and (the endothermic) dissolution of the Amino Pyridine, the vessel was charged with 12.5 L of N-methyl-2-pyrolidinone (12.8 kg, 5 vol). An addition funnel was charged with 1.8 L (0.6 equiv, 13.9 moles) phenyl chloroformate which was then added over 68 minutes to the solution of the Amino Pyridine keeping the internal temperature ≤30° C. The reaction was agitated for >30 minutes at an internal temperature of 20±5° C. The vessel was then charged with 61±1 g of seed as a slurry in 200 mL acetonitrile and aged for ≥30 min. The addition funnel was charged with 1.25 L (0.45 equiv, 9.7 moles) of phenyl chloroformate which was then added over 53 minutes to the reaction suspension while again keeping the temperature ≤30° C. The contents of the reactor were aged ≥30 hours at 20±5° C. After assaying the supernatant (≤15 mg/g for both product and starting material), the solids were filtered using an Aurora filter equipped with a 12 μm Teflon cloth. The mother liquor was forwarded to a $2^{nd}$ 60 L, glass-lined, jacketed reactor. The reactor and cake were rinsed with 1×10 L of 5:10 NMP/ACN and 1×10 L ACN. The washes were forwarded to the $2^{nd}$ reactor as well. The cake was dried under vacuum with a nitrogen bleed for ≥24 hours to afford 5.65 kg (90.2% yield) of the product, Phenyl Carbamate-HCl as an off-white solid in 98.8 wt % with 99.2% LCAP purity.

Phenyl (6-methylpyridin-3-yl)carbamate hydrochloride (Phenyl Carbamate-HCl) $^1H$ NMR (400 MHZ, DMSO-$d_6$) δ ppm 11.24 (s, 1H), 8.81 (s, 1H), 8.41 (d, 1 H, J=8.8 Hz), 7.85 (d, 1 H, J=8.8 Hz), 7.48-7.44 (m, 2H), 7.32-7.26 (m, 3H), 2.69 (s, 3H); $^{13}C$ NMR (100 MHz, DMSO-$d_6$) δ ppm 151.66, 150.01, 147.51, 136.14, 133.79, 129.99, 129.49, 127.75, 125.87, 121.70, 18.55: HR-MS: Calculated for $C_{13}H_{12}N_2O_2$: 228.0899, $M+H^+$=229.0972; Observed mass: 229.0961

Alternative Synthesis of Phenyl Carbamate HCl

5-Amino-2-methylpyridine (53.2 kg, 1.0 equiv) and acetonitrile (334 kg, 8.0 mL/g) were charged to a nitrogen flushed glass-lined reactor. The contents of the reactor were stirred while warming to 25-30° C. The mixture was then recirculated through a filter packed with activated carbon (11 kg, 20 wt %) for 3 h intervals while maintaining 25-30° C. Following each 3 h interval, a sample of the mixture was analyzed for color by comparison to a color standard and UV Absorbance at 440 nm. Once a satisfactory result was achieved, the filter was blown out into the reactor and the filter was rinsed with acetonitrile (85 kg, 2.0 mL/g). The acetonitrile rinse was transferred into the reaction mixture. 1-Methyl-2-pyrrolidinone (274 kg, 5.0 mL/g) was charged to the reaction mixture in the glass-lined reactor. Phenyl chloroformate (46.6 kg, 0.6 equiv) was slowly added to the mixture while maintaining 15-30° C. (typically 60-70 min). The reaction mixture was stirred for approximatly 60 minutes while maintaining 20-25° C. Phenyl (6-methylpyridin-3-yl) carbamate hydrochloride (0.58 kg, 0.010 equiv) seed crystals were charged to the stirring mixture. The slurry was then stirred for approximatly 4 h at 20±5° C. Phenyl chloroformate (33.4 kg, 0.45 equiv) was slowly added to the slurry while maintaining 15-30° C. The mixture was then allowed to age while stirring for 8±1 h whereupon concentration of 5-amino-2-methylpyridine (target ≤15 mg/mL) and phenyl (6-methylpyridin-3-yl)carbamate hydrochloride (target ≤15 mg/mL) were checked by HPLC. The batch was then filtered under vacuum and washed with a mixture of acetonitrile (112 kg, 2.68 mL/g) and 1-methyl-2-pyrrolidinone (72 kg, 1.32 mL/g) followed by washing thrise with acetonitrile (167 kg, 4.0 mL/g). The solids were deliquored followed by transfering to a tray dryer maintained between 20-40° C. and 1.3-0.65 psia until an LOD of <1 wt % was achieved, whereupon phenyl (6-methylpyridin-3-yl)carbamate hydrochloride 106.3 kg (81.6% yield) was isolated from the dryer.

Methyl 4-(3-amino-2-fluorobenzyl)piperazine-1-carboxylate (Piperazine Aniline)

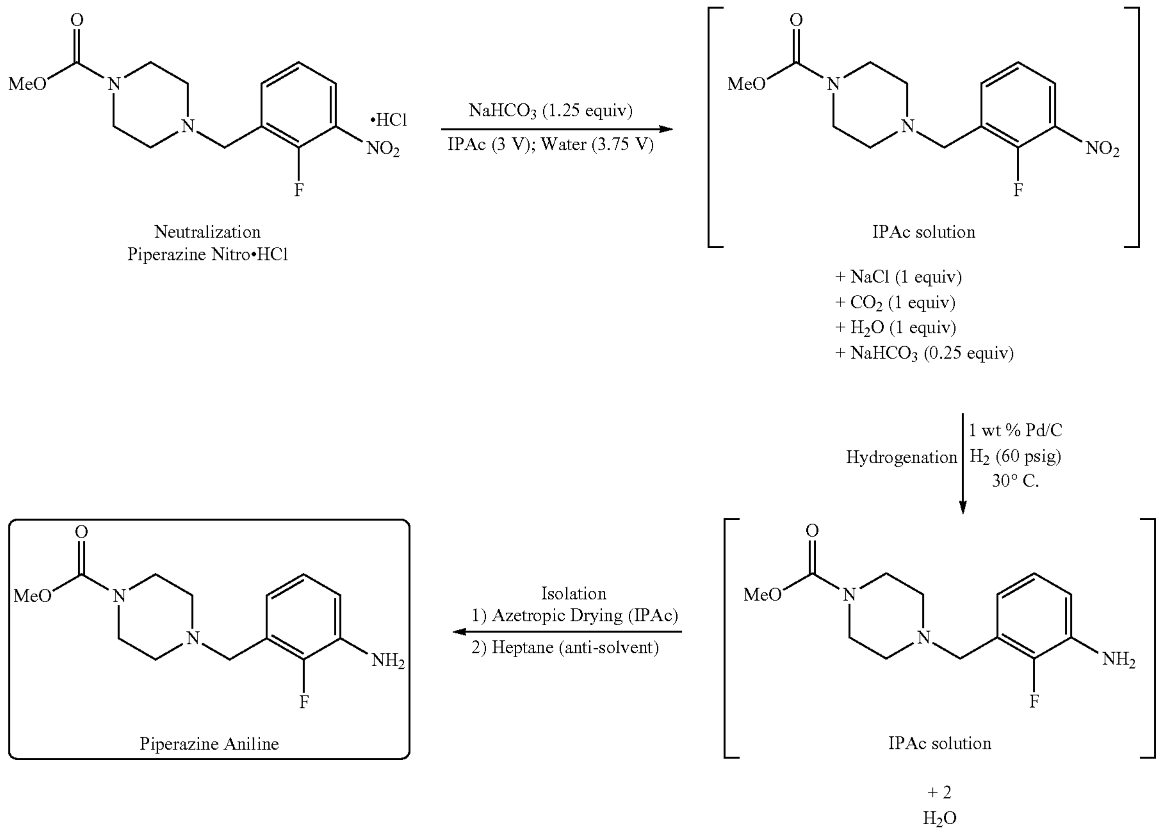

To a 100-L jacketed glass-lined reactor were added methyl 4-(2-fluoro-3-nitrobenzyl) piperazine-1-carboxylate hydrochloride (2.00 kg, 1.00 equiv) and isopropyl acetate (6.00 L, 3.00 Vol with-respect to starting material). The resulting slurry was agitated under a nitrogen sweep. To the mixture was added dropwise over 45±30 min: 7.7% w/w aqueous sodium bicarbonate solution (629 g, 1.25 equiv of sodium bicarbonate dissolved in 7.50 L water), maintaining an internal temperature of 20±5° C. by jacket control (NOTE: addition is endothermic, and may evolve up to 1 equiv of carbon dioxide gas). The mixture was stirred for ≥15 min, resulting in a clear biphasic mixture. Agitation was stopped and the layers were allowed to settle.

The bottom (aqueous) layer was drained and analyzed by pH paper to ensure that the layer is pH >6. Quantititative HPLC analysis of the upper (organic) layer revealed 97-100% assay yield of the methyl 4-(2-fluoro-3-nitrobenzyl)piperazine-1-carboxylate freebase (1.73-1.78 kg). The upper (organic) layer was transferred through an in-line filter into a 20-L Hastelloy® hydrogenator, and the 100-L reactor and lines were rinsed with an additional aliquot of isopropyl acetate (2.00 L, 1.00 Vol). The hydrogenator was purged with nitrogen and vented to atmospheric pressure. To the reaction mixture was added a slurry of 5.0 wt % palladium on carbon (20.0 g, Strem/BASF Escat™ 1421, approx 50% water) in isopropyl acetate (400 mL), followed by a 400 mL rinse. The resulting reaction mixture was diluted with an additional aliquot of isopropyl acetate (1.2 L; total isopropyl acetate amount is 10.0 L, 5.00 Vol). The hydrogenator was purged three times with nitrogen (pressurized to 60±10 psig, then vented to atmospheric pressure), then pressurized to 60±5 psig with hydrogen. The reaction mixture was stirred at <100 rpm at 30±5° C. while maintaining 60±5 psig hydrogen, for >2 hours until reaction was deemed complete. This temperature and pressure correspond to a measured kLa value of approx 0.40 in a 20-L Hydrogenator. End of reaction is determined by dramatic decrease in hydrogen consumption accompanied by a relief in the heat evolution of the reaction. To control potential dimeric impurities, the reaction is continued for at least 30 minutes after this change in reaction profile, and HPLC analysis is performed to confirm that >99.5% conversion of the hydroxyl-amine to the aniline is achieved.

At the end of reaction, the hydrogenator was purged with nitrogen twice (pressurized to 60±10 psig, then vented to atmospheric pressure). The crude reaction mixture was filtered through a 5 um filter followed by a 0.45 μm filter in series, into a 40-L glass-lined reactor. The hydrogenator and lines were washed with an additional aliquot of isopropyl acetate (2.00 L). Quantitative HPLC analysis of the crude reaction mixture revealed 95-100% assay yield (1.52-1.60 kg aniline product). The reaction mixture was distilled under reduced pressure (typically 250-300 mbar) at a batch temperature of 50±5° C. until the total reaction volume was approximately 8.00 L (4.00 Vol). The batch was subjected to a constant-volume distillation at 50±5° C., 250-300 mbar, by adding heptane to control the total batch volume. After approximately 8.00 L (4.00 Vol) of heptane were added, GC analysis indicated that the solvent composition was approximately 50% isopropyl acetate, 50% heptane. Vacuum was broken, and the internal batch temperature was maintained at 50±5° C. To the reaction mixture was added a slurry of seed (20.0 grams of product methyl 4-(3-amino-2-fluorobenzyl)piperazine-1-carboxylate, in a solvent mixture of 80 mL heptane and 20 mL isopropyl acetate). The resulting slurry was allowed to stir at 50±5° C. for 2±1 hours, then cooled to 20±5° C. over 2.5±1.0 h. Additional heptane (24.0 L, 12.0 Vol) was added dropwise over 2 hours, and the batch was allowed to stir at 20±5° C. for ≥1 hours (typically overnight). Quantitative HPLC analysis of this filtered supernatant revealed <5 mg/mL product in solution, and the product crystals were 50-400 μm birefringent rods. The reaction slurry was filtered at 20° C. onto a filter cloth, and the cake was displacement-washed with heptane (6.00 L, 2.00 Vol). The cake was dried on the filter under nitrogen sweep at ambient temperature for >4 hours, until sample dryness was confirmed by LOD analysis (indicated <1.0 wt % loss). The product methyl 4-(3-amino-2-fluorobenzyl) piperazine-1-carboxylate (1.56 kg) was isolated as a pale-yellow powder in 86% yield at 99.8 wt % by HPLC with 100.0 $LCAP_{210}$. [Analysis of the combined filtrates and washes revealed 108 grams (7.0%) of product lost to the mother liquors. The remaining mass balance is comprised of product hold-up in the reactor (fouling).] $^1$H NMR (DMSO-$d_6$, 400 MHz) δ:6.81 (dd, J=7.53, 7.82 Hz, 1H), 6.67 (m, 1H), 6.49 (m, 1H), 5.04 (s, 2H), 3.58 (s, 3H), 3.45 (m, 2H), 3.34 (m, 4H), 2.33 (m, 4H). $^{19}$F NMR ($d_6$-DMSO, 376 MHz) δ: −140.2. $^{13}$C NMR ($d_6$-DMSO, 125 MHz) δ: 155.0, 150.5, 148.2, 136.2 (m), 123.7 (m), 117.6, 115.1, 73.7, 54.9 (m), 52.1 (m), 43.4. mp=89.2° C.

Alternate Route to Piperazine Aniline

To a jacketed glass-lined reactor were added methyl 4-(2-fluoro-3-nitrobenzyl)piperazine-1-carboxylate hydrochloride (46.00 kg, 1.00 equiv) and isopropyl acetate (200 kg, 5.0 mL/g). The resulting slurry was agitated under a nitrogen sweep. To the mixture was added 7.4% w/w aqueous sodium bicarbonate solution (1.25 equiv) while maintaining an internal temperature of 25±5° C. The mixture was agitated for ≥30 min, resulting in a clear biphasic mixture. Agitation was stopped and the bottom (aqueous) layer was discharged. Analysis of aqueous layer indicates pH ≥6. Water (92 kg, 2.0 mL/g) was charged the organic layer and agitated for ≥15 min. Agitation was then stopped and the bottom (water wash) layer was discharged. Water (92 kg, 2.0 mL/g) was charged the organic layer and agitated for ≥15 min. Agitation was then stopped and the bottom (water wash) layer was discharged. The batch was distilled under reduced pressure while maintaining the batch temperature between 40-50° C. The batch volume was held constant throughout the distillation by the continuous addition of isopropyl acetate. Once the water content of the batch was <1,500 ppm, the solution was passed through an inline filter into a Hastelloy reactor containing 5.0 wt % palladium on carbon (BASF Escat 1421, 0.69 kg, 1.5 wt %). The jacketed glass-lined reactor was rinsed with isopropyl acetate (100 kg, 2.5 mL/g) and added to the Hastelloy reactor though the inline filter.

The batch was adjusted to approximately 25-35° C. (preferably 30° C.) and hydrogen gas was added to maintain about 4 barg with vigorous agitation. Hydrogenation was continued for 1 h after hydrogen uptake has ceased, and ≥99.0% conversion by HPLC were achieved. The palladium on carbon catalyst was collected by filtration and the supernatant was collected in a reactor. Isopropyl acetate (40 kg, 1.0 mL/g) was charged to the Hastelloy reactor and transferred through the filter and collected in the jacketed glass-lined reactor.

The batch was concentrated under reduced pressure while maintaining the batch temperature between 35-55° C. until the final volume was approximately 4.0 mL/g. Heptane (219 kg, 7.0 mL/g) was added to the jacketed glass-lined reactor while maintaining the batch between 50-60° C., until 20-25% isopropyl acetate in heptane was achieved as measured by GC. The solution was cooled to between 40-50° C. and seeded with methyl 4-(3-amino-2-fluorobenzyl)piperazine-1-carboxylate (0.46 kg, 1.0 wt %) as a slurry in heptane (6.4 kg, 0.20 mL/g). The slurry was aged for approximately 2 h, whereupon, the batch was distilled under reduced pressure while maintaining the batch temperature between 35-45° C. The batch volume was held constant throughout the distillation by the continuous addition of heptane (219 kg, 7.0 mL/g). The batch was then cooled to between 15-25° C. over approximately 3 h. Concentration of the supernatant was measured to be ≤5 mg/mL methyl 4-(3-amino-2-fluorobenzyl)piperazine-1-carboxylate by HPLC.

The batch was filtered and the resulting solids were successively washed with heptane (63 kg, 2.0 mL/g) then heptane (94 kg, 3.0 mL/g). The solids were dried on the filter with a stream of dry nitrogen with vacuum until an LOD of ≤1 wt % was achieved whereupon 33.88 kg (90.7% yield) was isolated from the filter dryer.

Omecamtiv Mecarbil Dihydrochloride Hydrate Procedure

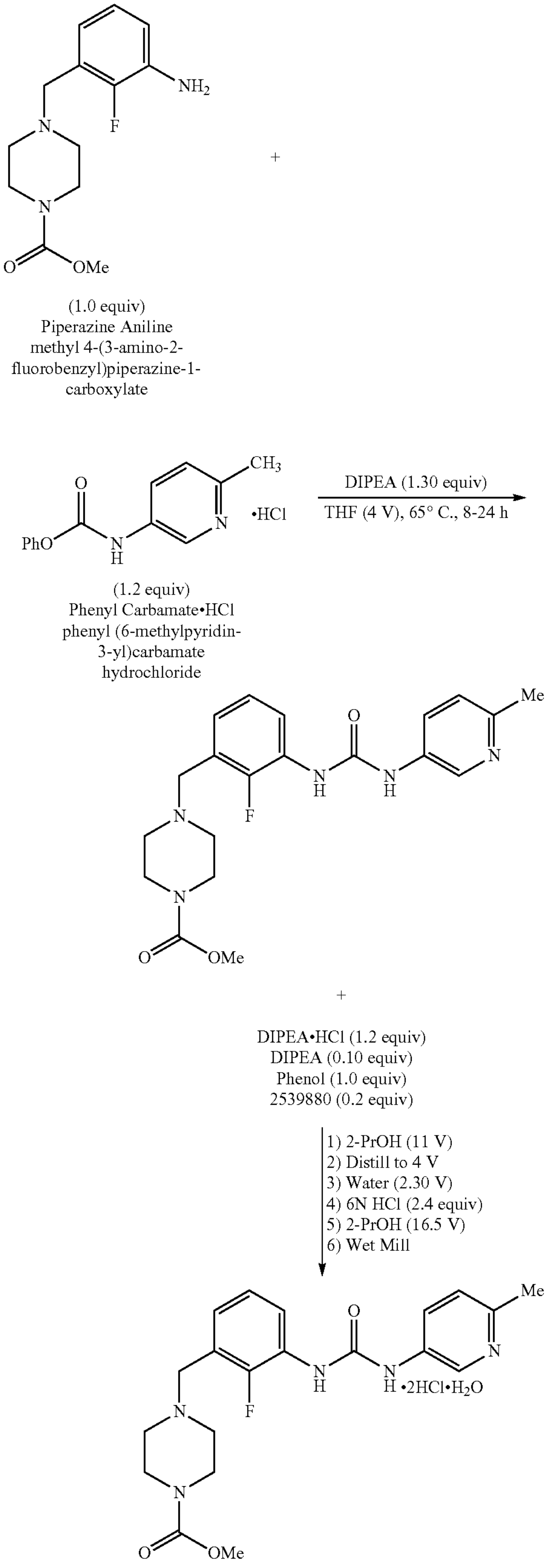

To a 15 L glass lined reactor were charged methyl 4-(3-amino-2-fluoro-benzyl)piperazine-1-carboxylate (1,202 g, 4.50 mol), phenyl (6-methylpyridin-3-yl)carbamate hydrochloride (1,444 g, 5.40 mol), and tetrahydrofuran (4.81 L). The resulting slurry was agitated under a nitrogen sweep and N,N-diisopropylethylamine (1,019 L, 5.85 mol) was then charged to the slurry which resulted in a brown solution. The temperature of the solution was increased to 65° C. and agitated for 22 h, until <1% AUC piperazine aniline remained by HPLC analysis.

The batch was cooled to 50° C. and distilled under reduced pressure while maintaining the internal temperature of the vessel below 50° C. by adjusting vacuum pressure. 2-Propanol was added with residual vacuum at a rate to maintain a constant volume in the 15 L reactor. A total of 10.5 kg of 2-propanol was required to achieve <5% THF by GC. Water (2.77 kg) was then charged to the reactor followed by the addition of 6N HCl (1.98 kg) at a rate to maintain the internal temperature below 60° C. The reactor was brought to ambient pressure under a nitrogen sweep. The solution was then heated to 60° C., and transferred to a 60 L glass lined reactor through an inline filter. The 15 L reactor was then rinsed with 1:1 water/2-propanol (1.2 L) which was sent through the inline filter to the 60 L reactor.

The 60 L reactor was adjusted to 45° C. and a slurry of seed (114 g, 0.23 mol) in 2-propanol (0.35 L) was added to the reactor resulting in a slurry. The batch was aged at 45° C. for 1 h, followed by the addition of 2-propanol (3.97 kg) through an inline filter over 2 h. The batch was heated to 55° C. over 1 h and held for 0.25 h, then cooled back to 45° C. over 1 h and held overnight at 45° C. 2-propanol (11.71 kg) was then added through an inline filter to the batch over 3 h. The batch was aged for 1 h and then cooled to 20° C. over 2 h and held at 20° C. for 0.5 h. The batch was then recirculated though a wet mill affixed with 1-medium and 2-fine rotor-stators operating at 56 Hz for 2.15 h, until no further particle size reduction was observed by microscopy.

The batch was then filtered through a 20" Hastelloy® filter fitted with a 12 μm filter cloth under 500 torr vacuum. A wash solution of 95:5 2-propanol: water (1.82 L) was charged through an inline filter to the 60 L reactor, then onto the filter. A second wash of 2-propanol (2.85 L) was charged through an inline filter to the 60 L reactor, then onto the filter. The batch was then dried under 5 psi humidified nitrogen pressure until <5,000 ppm 2-propanol, and 2.5-5% water remained. The final solid was discharged from the filter to afford 2.09 kg of methyl 4-(2-fluoro-3-(3-(6-methylpyridin-3-yl)ureido)benzyl)piperazine-1-carboxylate as an off-white crystalline solid in 89% yield at 99.88 wt % by HPLC, 100.0% AUC. Total losses to liquors was 0.10 kg (4.7%).

DSC: $T_{onset}$=61.7° C., $T_{max}$=95.0° C.; TGA=2.2%, degradation onset=222° C.; $^1$H HMR ($D_2O$, 500 MHz) δ 8.87 (s, 1H), 8.18 (d, J=8.9 Hz, 1H), 7.83 (t, J=7.5 Hz, 1H), 7.71 (d, J=8.8 Hz, 1H), 7.35-7.29 (m, 2H), 4.48 (s, 2H), 4.24 (br s, 2H), 3.73 (s, 3H), 3.31 (br s, 6H), 2.68 (s, 3H); $^{13}$C HMR ($D_2O$, 150 MHz) δ 156.8, 154.2, 153.9 (J=249 Hz), 147.8, 136.3, 136.1, 130.1, 129.4, 128.0, 127.2, 125.5 (J=11.8 Hz), 125.1 (J=4.2 Hz), 116.1 (J=13.5 Hz), 53.54, 53.52, 53.49, 50.9, 40.5, 18.2.

Alternative Process for the Coupling (Aniline Phenyl Carbamate)

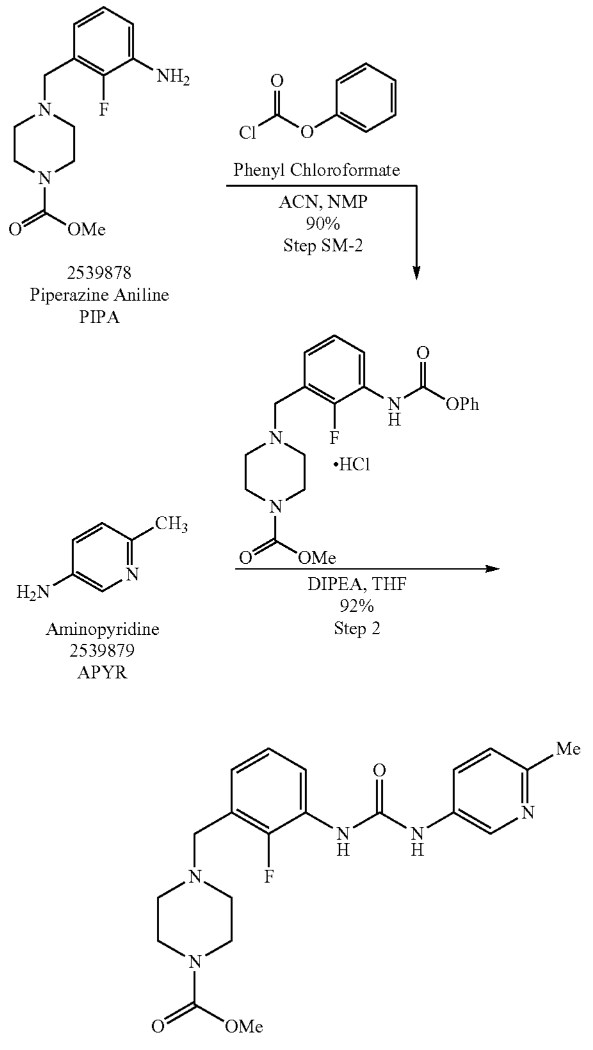

AMG 423

A reaction vessel was charged methyl 4-(3-amino-2-fluorobenzyl)piperazine-1-carboxylate (2.5 g, 1.0 equiv), acetonitrile (25.0 mL, 10.0 mL/g) and 1-methyl-2-pyrrolidinone (12.5 mL, 5.0 mL/g). The batch was cooled to 0° C. whereupon phenyl chloroformate (1.20 mL, 1.02 equiv) was added over approximately 5 min. After 45 minutes the resulting slurry resulted was allowed to warm to 20° C. The solids were collected by filtration and rinsed twice with acetonitrile (10.0 mL, 4.0 mL/g). The solids were dried under a stream of dry nitrogen to afford methyl 4-(2-fluoro-3-((phenoxycarbonyl)amino)benzyl)piperazine-1-carboxylate hydrochloride 2.8 g (71% yield) as a white solid.

4-(2-fluoro-3-((phenoxycarbonyl)amino)benzyl)piperazine-1-carboxylate hydrochloride: $^1H$ NMR (400 MHz, DMSO-$d_6$) δ ppm 3.08 (br. s., 2H), 3.24-3.52 (m, 4H), 3.62 (s, 3H), 4.03 (d, J=11.25 Hz, 2H), 4.38 (br. s., 2H), 7.11-7.35 (m, 4H), 7.35-7.49 (m, 2H), 7.49-7.66 (m, 1H), 7.80 (s, 1H), 10.12 (br. s, 1H), 11.79 (br. s, 1H); HRMS=388.1676 found, 388.1667 calculated.

A reaction vessel was charged methyl 4-(2-fluoro-3-((phenoxycarbonyl)amino)benzyl)piperazine-1-carboxylate hydrochloride (0.50 g, 1.0 equiv), 6-methylpyridin-3-amine (0.15 g, 1.2 equiv), tetrahydrofuran (2.0 mL, 4.0 mL/g) and N,N-diisopropylethylamine (0.23 mL, 1.1 equiv). The batch was heated to 65° C. for 22 h, whereupon quantitative HPLC analysis indicated 0.438 g (92% assay yield) of omecamtiv mecarbil.

Alternative Omecamtiv Mecarbil Dihydrochloride Hydrate Procedure

Omecamtiv Mecarbil, free base (3.0 kg, 1.0 equiv) was charged to a nitrogen purged jacketed vessel followed by water (4.6 L, 1.5 mL/g) and 2-propanol (6.1 L, 2.60 mL/g). The slurry was agitated and heated to approximately 40° C., whereupon 6N HCl (2.6 L, 2.10 equiv) was charged to the slurry resulting in a colorless homogenous solution. The solution was heated to between 60-65° C. and transferred through an inline filter to a 60 L reactor pre-heated to 60° C. The batch was cooled to 45° C. whereupon Omecamtiv Mecarbil dihydrochloride hydrate (150 g, 5.0 wt %) was charged to the vessel as a slurry in 95:5 (v/v) 2-Propanol/Water (600 mL, 0.20 mL/g). The resulting slurry was maintained at 45° C. for 0.5 h followed by cooling to approximately 20° C. then held for 3-16 h. 2-Propanol (33.0 L, 11.0 mL/g) was added over ≥2h followed by a ≥1 h isothermal hold at approximately 20° C. (Supernatant pH ≤7).

The batch was recirculated through a wet mill for 5-10 batch turnovers until sufficient particle reduction was achieve as compared to offline calibrated visual microscopy reference. The slurry was filtered by vacuum and the resulting solids were washed with two washes of 95:5 (v/v) 2-Propanol/Water (3.0 L, 1.0 mL/g) and a final cake wash with 2-Propanol (6.0 L, 2.0 mL/g). The cake was dried on the filter by pushing humidified nitrogen through the cake until ≤5,000 ppm 2-propanol and 2.5-5% water were measured by GC and KF analysis, respectively. Omecamtiv Mecarbil dihydrochloride hydrate was isolated as a colorless crystalline solid (3.40 kg, 93% yield).

pH Dependent Release Profiles

A formulation of omecamtiv mecarbil hemihydrate (free base) and dihydrochloride hydrate (Form A) were prepared having the following components, all components reported as a w/w %:

Free Base (75 mg matrix tablet) Active granulation: 15.37% free base; 30% hypromellose, HPMC K100 MPrem CR; 10% citric acid monohydrate; 11.88% microcrystalline cellulose, Avicel PH 101; 6.75% lactose monohydrate, FastFlo 316; 12.5% purified water; and Citric Acid granulation: 20% citric acid monohydrate; 5% microcrystalline cellulose, Avicel PH 101; and 1% magnesium stearate, non-bovine.

Form A (75 mg matrix tablet) Intra-granulation: 18.37% Form A; 30% hypromellose, HPMC K100 MPrem CR; 0.50% magnesium stearate;; and Extra-granulation: 16.88% microcrystalline cellulose, Avicel PH 101; 18.37% citric acid anhydrous; and 0.5% magnesium stearate, non-bovine.

The formulations were tested at pH 2 and pH 6.8 and the amount of drug released over time was measured. The results of this drug release profile are shown in FIG. 6.

The foregoing is merely illustrative of the invention and is not intended to limit the invention to the disclosed salts or polymorphs. Variations and changes which are obvious to one skilled in the art are intended to be within the scope and nature of the invention which are defined in the appended claims.

What is claimed is:

1. A method of preparing omecamtiv mecarbil free base

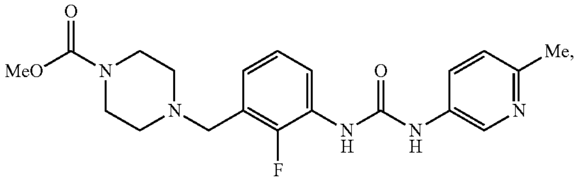 [SMILES: COC(=O)N1CCN(Cc2cccc(NC(=O)Nc3ccc(C)nc3)c2F)CC1]

comprising:

admixing methyl 4-(3-amino-2-fluorobenzyl) piperazine-1-carboxylate (Piperazine Aniline)

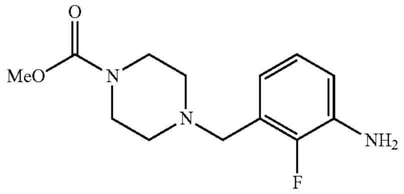 [SMILES: COC(=O)N1CCN(Cc2cccc(N)c2F)CC1]

and phenyl (6-methylpyridin-3-yl)carbamate hydrochloride (Phenyl Carbamate·HCl)

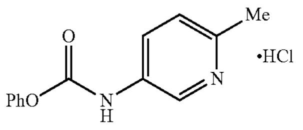 [SMILES: Cc1ccc(NC(=O)Oc2ccccc2)cn1 ; Cl]

in the presence of diisopropylethylamine and tetrahydrofuran.

2. The method of claim 1, wherein the phenyl (6-methylpyridin-3-yl)carbamate hydrochloride (Phenyl Carbamate·HCl)

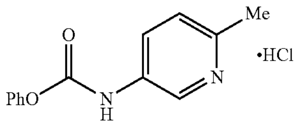 [SMILES: Cc1ccc(NC(=O)Oc2ccccc2)cn1 ; Cl]

is prepared by admixing Amino Pyridine

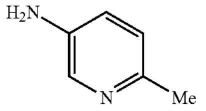

with phenyl chloroformate in acetonitrile and N-methyl-2-pyrrolidinone.

3. The method of claim 1, wherein the methyl 4-(3-amino-2-fluorobenzyl) piperazine-1-carboxylate (Piperazine Aniline)

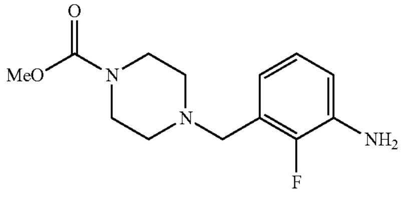 [SMILES: COC(=O)N1CCN(Cc2cccc(N)c2F)CC1]

is prepared by a process comprising:

step (i) neutralizing methyl 4-(2-fluoro-3-nitrobenzyl) piperazine-1-carboxylate hydrochloride (Piperazine Nitro·HCl)

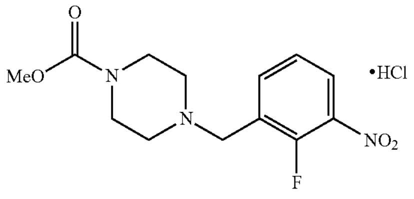 [SMILES: COC(=O)N1CCN(Cc2cccc([N+](=O)[O-])c2F)CC1 ; Cl]

with sodium bicarbonate in water and isopropyl acetate to yield methyl 4-(2-fluoro-3-nitrobenzyl) piperazine-1-carboxylate

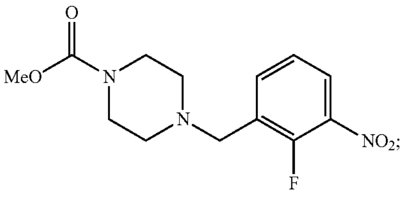 [SMILES: COC(=O)N1CCN(Cc2cccc([N+](=O)[O-])c2F)CC1]

step (ii) hydrogenating methyl 4-(2-fluoro-3-nitrobenzyl) piperazine-1-carboxylate in the presence of palladium on carbon in isopropyl acetate to form methyl 4-(3-amino-2-fluorobenzyl) piperazine-1-carboxylate; and step (iii) isolating 4-(3-amino-2-fluorobenzyl) piperazine-1-carboxylate from isopropyl acetate and heptane.

4. The method of claim 3, wherein the methyl 4-(2-fluoro-3-nitrobenzyl) piperazine-1-carboxylate hydrochloride

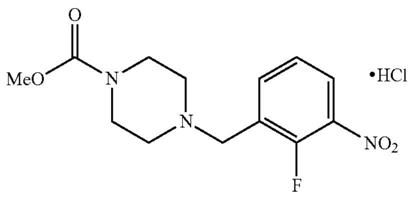 [SMILES: COC(=O)N1CCN(Cc2cccc([N+](=O)[O-])c2F)CC1 ; Cl]

is prepared by a process comprising:

step (i) admixing 2-fluoro-3-nitrotoluene (FN-Toluene)

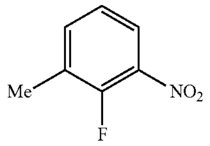 [SMILES: Cc1cccc([N+](=O)[O-])c1F]

with N-bromosuccinimide, benzoyl peroxide, and acetic acid to form a mixture;

step (ii) contacting the mixture from step (i) with diethylphosphite and diisopropylethylamine in methanol to form a solution of FN-bromide

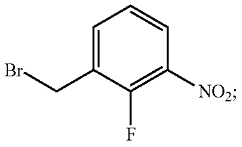 [SMILES: O=[N+]([O-])c1cccc(CBr)c1F]

step (iii) admixing the solution of FN-bromide from step (ii) with diisopropylethylamine, and piperazine carboxylate

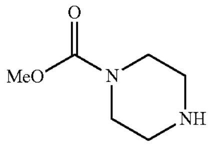

in toluene to form a solution of Piperazine Nitro free base

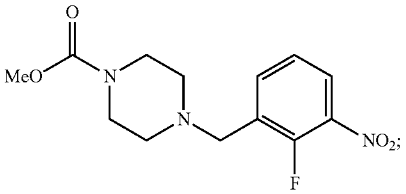 [SMILES: COC(=O)N1CCN(Cc2cccc([N+](=O)[O-])c2F)CC1]

and step (iv) admixing the solution of Piperazine Nitro free base with IPA, water, and HCl to form methyl 4-(2-fluoro-3-nitrobenzyl) piperazine-1-carboxylate hydrochloride.

5. A method of preparing omecamtiv mecarbil free base

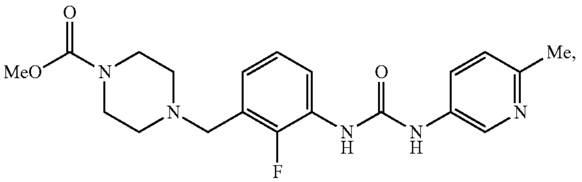 [SMILES: COC(=O)N1CCN(Cc2cccc(NC(=O)Nc3ccc(C)nc3)c2F)CC1]

comprising:

step (i) admixing 2-fluoro-3-nitrotoluene (FN-Toluene)

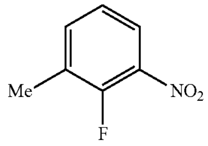 [SMILES: Cc1cccc([N+](=O)[O-])c1F]

with N-bromosuccinimide, benzoyl peroxide, and acetic acid to form a mixture;

step (ii) contacting the mixture from step (i) with diethylphosphite and diisopropylethylamine in methanol to form a solution of FN-bromide

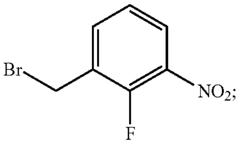 [SMILES: O=[N+]([O-])c1cccc(CBr)c1F]

step (iii) admixing the solution of FN-bromide from step (ii) with diisopropylethylamine and piperazine carboxylate

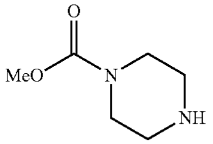

in toluene to form a solution of Piperazine Nitro free base

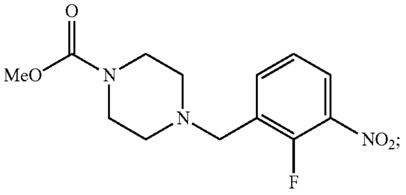 [SMILES: COC(=O)N1CCN(Cc2cccc([N+](=O)[O-])c2F)CC1]

and step (iv) admixing the solution of Piperazine Nitro free base with IPA, water, and HCl to form methyl 4-(2-fluoro-3-nitrobenzyl) piperazine-1-carboxylate hydrochloride (Piperazine Nitro·HCl)

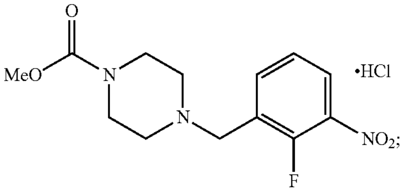 [SMILES: COC(=O)N1CCN(Cc2cccc([N+](=O)[O-])c2F)CC1 ; Cl]

wherein the method further comprises:

step (v) neutralizing the Piperazine Nitro·HCl with sodium bicarbonate in water and isopropyl acetate to yield methyl 4-(2-fluoro-3-nitrobenzyl) piperazine-1-carboxylate

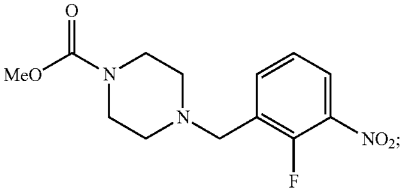 [SMILES: COC(=O)N1CCN(Cc2cccc([N+](=O)[O-])c2F)CC1]

step (vi) hydrogenating methyl 4-(2-fluoro-3-nitrobenzyl) piperazine-1-carboxylate in the presence of palladium on carbon in isopropyl acetate to form methyl 4-(3-amino-2-fluorobenzyl) piperazine-1-carboxylate; and step (vii) isolating 4-(3-amino-2-fluorobenzyl) piperazine-1-carboxylate from isopropyl acetate and heptane, to form methyl 4-(3-amino-2-fluorobenzyl) piperazine-1-carboxylate (Piperazine Aniline)

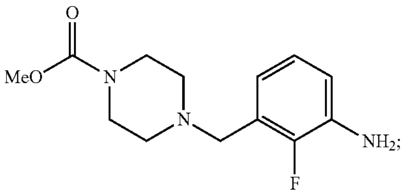

wherein the method further comprises:

step (viii) admixing Amino Pyridine

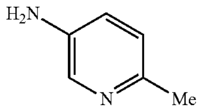

with phenyl chloroformate in acetonitrile and N-methyl-2-pyrrolidinone to form phenyl (6-methylpyridin-3-yl)carbamate hydrochloride (Phenyl Carbamate·HCl)

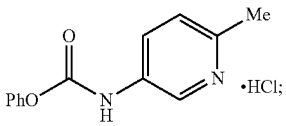 [SMILES: Cc1ccc(NC(=O)Oc2ccccc2)cn1]

and step (ix) admixing the Piperazine Aniline and the Phenyl Carbamate·HCl in the presence of diisopropylethylamine and tetrahydrofuran to form the omecamtiv mecarbil free base.

6. The method of claim 3, wherein the hydrogenating of step (ii) is in the presence of 5.0 wt % palladium on carbon.

7. The method of claim 3, wherein the hydrogenating of step (ii) is in a hydrogenator pressurized to 60±5 psig with hydrogen.

8. The method of claim 3, wherein the hydrogenating of step (ii) is at a temperature of 30±5° C.

* * * * *